(12) United States Patent
Yeung et al.

(10) Patent No.: US 11,807,900 B2
(45) Date of Patent: Nov. 7, 2023

(54) SYSTEMS AND METHODS FOR PRE-ANALYTICAL SUBSTRATE PROCESSING

(71) Applicant: GENOMIC HEALTH, INC., Redwood City, CA (US)

(72) Inventors: Hubert Yeung, Millbrae, CA (US); Amy Lee Hsieh Yuan, Saratoga, CA (US); Chun Wai Lee, El Cerrito, CA (US); Gabriel Jesus Samuel Perlas Moraleda, Santa Clara, CA (US); Jonathan M. Cassel, Half Moon Bay, CA (US)

(73) Assignee: Genomic Health, Inc., Redwood City, CA (US)

( * ) Notice: Subject to any disclaimer, the term of this patent is extended or adjusted under 35 U.S.C. 154(b) by 336 days.

(21) Appl. No.: 16/449,075

(22) Filed: Jun. 21, 2019

(65) Prior Publication Data

US 2019/0390252 A1  Dec. 26, 2019

Related U.S. Application Data

(60) Provisional application No. 62/821,371, filed on Mar. 20, 2019, provisional application No. 62/687,887, filed on Jun. 21, 2018.

(51) Int. Cl.
| | | |
|---|---|---|
| C12Q 1/68 | (2018.01) | |
| C12Q 1/686 | (2018.01) | |
| C12Q 1/6806 | (2018.01) | |
| C12Q 1/6809 | (2018.01) | |
| C12Q 1/6865 | (2018.01) | |
| C12Q 1/6813 | (2018.01) | |

(52) U.S. Cl.
CPC ........... *C12Q 1/686* (2013.01); *C12Q 1/6806* (2013.01); *C12Q 1/6809* (2013.01); *C12Q 1/6813* (2013.01); *C12Q 1/6865* (2013.01); *C12Q 2523/115* (2013.01); *C12Q 2523/301* (2013.01); *C12Q 2523/305* (2013.01); *C12Q 2523/31* (2013.01)

(58) Field of Classification Search
None
See application file for complete search history.

(56) References Cited

U.S. PATENT DOCUMENTS

| | | | |
|---|---|---|---|
| 5,998,129 A | 7/1999 | Schutze et al. | |
| 6,669,685 B1 * | 12/2003 | Rizoiu | A61B 18/20 604/22 |
| 7,429,731 B1 | 9/2008 | Karpetsky | |
| 9,546,935 B1 | 1/2017 | Astle | |
| 2008/0206870 A1 | 8/2008 | Groisman et al. | |
| 2010/0028978 A1 * | 2/2010 | Angros | B01L 3/0293 435/283.1 |
| 2012/0137792 A1 | 6/2012 | Bunker et al. | |
| 2013/0109024 A1 * | 5/2013 | Rajagopalan | G01N 1/31 435/6.12 |
| 2013/0334343 A1 | 12/2013 | Bunker et al. | |
| 2014/0273087 A1 | 9/2014 | Morris | |
| 2015/0045232 A1 | 9/2015 | Han et al. | |
| 2016/0243026 A1 * | 8/2016 | Pathak | A61K 9/1658 |
| 2017/0131303 A1 | 5/2017 | Reinhardt et al. | |

FOREIGN PATENT DOCUMENTS

| | | |
|---|---|---|
| JP | 2000146782 A | 5/2000 |
| JP | 2016128823 A | 7/2016 |
| KR | 1020150107374 A | 9/2015 |
| WO | 2014054016 A1 | 4/2014 |
| WO | WO-2014054016 A1 * | 4/2014 ............... G01N 1/28 |

OTHER PUBLICATIONS

Burgemeister et al. (Path Res Pract, 2003, 199:431-436) (Year: 2003).*
Waters—The Science of What's Possible. "HPLC Columns: State-of-the-art Reversed-Phase and HILIC HPLC Columns" (2019)—retrieved on Dec. 16, 2019 from the following link: https://www.waters.com/waters/en_US/HPLC-Columns-C18-Amide-C4-C8-SEC-HILIC-Phenyl-T3-Shield-RP18-C18%2B/nav.htm?cid=511505&xcid=ext586&gclid=EAlalQobChMI_aaY85nJ5QIVVh-tBh0bbwLtEAAYASAAEgKBv_D_BwE&locale=en_US.
KIPO, Notification of and International Search Report and Written Opinion dated Oct. 8, 2019 in International (PCT) Application No. PCT/US2019/038558 (13 pages).
KIPO, Notification of and International Search Report and Written Opinion dated Oct. 18, 2019 in related International (PCT) Application No. PCT/US2019/038581 (13 pages).
Hamilton Company, "Genomics," obtained online on Dec. 16, 2019 from link—https://www.hamiltoncompany.com/automation/genomics.
Nederman, "Dust free blasting unit 418A/460A," obtained online on Dec. 16, 2019 from link—https://www.nederman.com/en/products/mobile-filters-and-compact-units/industrial-vacuum-cleaner/dust-free-blasting-unit-418a460a/c-24/c-1675/p-89076.
Qiagen, "Neuclic Acid Extraction," obtained online on Dec. 16, 2019 from link—https://www.qiagen.com/us/applications/ngs/mdx-ngs-genereader/nucleic-acid-extraction/.
Roche, "Avenio Millisect System," obtained online on Dec. 16, 2019 from link—https://sequencing.roche.com/en/products-solutions/by-category/sample-collection/avenio-millisect-system.html.

(Continued)

*Primary Examiner* — Stephanie K Mummert
(74) *Attorney, Agent, or Firm* — Casimir Jones, S.C.; Brian F. Bradley

(57) ABSTRACT

Some embodiments presented in this disclosure concern an Automated Tissue Dissection (ATD) System. An ATD system is a one stop, and potentially low-cost, system to perform dissections on a substrate from pathologist digital mark or pen mark on the substrate using non-contact and/or mechanical method to extract a Formalin-Fixed Paraffin-Embedded (FFPE) tissue sample with: (a) only the ROI or ROIs as area to be saved; and (b) remove or decompose nucleic acid content in the region of no interest (RONI) and collect all tissue sample from a standard microscope substrate into a specific container.

17 Claims, 12 Drawing Sheets

(56) References Cited

OTHER PUBLICATIONS

Thermo Fisher Scientific, "ArcturusXT(tm) Laser Capture Microdissection (LCM) System," obtained online on Dec. 16, 2019 from link—https://www.thermofisher.com/us/en/home/life-science/gene-expression-analysis-genotyping/laser-capture-microdissection/arcturus-laser-capture-microdissection-lcm-instrument.hlml.

* cited by examiner

SYSTEMS AND METHODS FOR PRE-ANALYTICAL SUBSTRATE PROCESSING

CROSS-REFERENCE TO RELATED APPLICATIONS

This application claims the benefit of priority under 35 U.S.C. § 119 from U.S. Provisional Patent Application 62/687,887 filed Jun. 21, 2018, and from U.S. Provisional Patent Application 62/821,371 filed Mar. 20, 2019, each of which is incorporated herein by reference in its entirety

FIELD

The present disclosure generally relates to fields of histology and/or pathobiology. More specifically, the present disclosure relates to pre-analytical substrate processing systems and related methods which, in some embodiments, may be useful for separating and isolating regions of interest (ROI) and regions of non-interest (RONI) in the substrate, e.g., biological substrates such as histology specimen.

BACKGROUND

A variety of methods have been suggested to resolve cumbersome nature of scraping procedures for preparation and/or processing of histological samples for downstream analysis. For example, vacuum blasting techniques have been recommended; however, these are only deployable in an industrial setting and thus require expensive tools and instruments. Also, currently there is no vacuum blasting technology that is compatible with substrates mounted on microscopic glass slides. Similarly, particle-based blasting methods such as sandblasting, e.g., with silica particles, silica-coated particles or polymer-coated ferromagnetic beads, require separation of the particles from the regions of interest (ROI) prior to implementation of the downstream analytical steps.

Current tissue dissection processes are completely manual, using razor blades to directly collect "S" (i.e., ROI) areas from substrates. For example, conventional workflows for substrate submissions include an entirely manual process where a user manually transfers pathologist area of interest markings on a stained slide to unstained slides using a standard off-the-shelf marking pen. The user then uses a razor blade or equivalent to scrape off the area of interest on the marked unstained substrate and collect into a container.

This described manual process limits operator accuracy by completely relying on operator hand/eye coordination, which affects the consistency and accuracy of the tissue scraping. This process also introduces ergonomics/safety issues because constant force being applied to the glass surface may cause laceration and ergonomic issues (e.g., carpel tunnel) with the operator.

Current implementations of digital pathology have improved many areas of histology/pathology workflows. However, there are still some important areas of unmet needs. One unmet need is that some substrate submissions cannot be processed digitally using the commercial Digital Pathology Systems. A substantial number of cases still require manual glass workflow processing. Therefore, there exists a need for a way to convert this process to achieve full digital workflow.

SUMMARY

Some embodiments presented in this disclosure concern an Automated Tissue Dissection (ATD) System. An ATD system is a one stop, and potentially low-cost, system to perform dissections on a substrate from pathologist digital mark or pen mark on the substrate using non-contact and/or mechanical method to extract a Formalin-Fixed Paraffin-Embedded (FFPE) tissue sample with: (a) only the ROI or ROIs as area to be saved; and (b) remove or decompose nucleic acid content in the region of no interest (RONI) and collect all tissue sample from a standard microscope substrate into a specific container.

According to certain aspects of the present disclosure, ATD is merged with a digital pathology process to scrape ROI on substrates. Also disclosed are systems and methods for either collecting desirable "S" (i.e., ROI) regions or removing undesired "X" regions in feasible ways. The described systems and methods provide a low cost flexible system to digitalize slide images and simplify downstream scraping processes.

The systems, in some embodiments, may be able to perform the following: (a) capture stained and unstained slide images with suitable magnification, (b) digitalize a pen marking into a digital marking, (c) perform an object based or other algorithm to match marking coordinates on a substrate to the associated substrates, (d) extract marked sample ROI into a container, (e) remove samples in RONI or decompose nucleic acid in RONI and collect all samples (e.g., tissue) into a container, and (f) lyse the sample and output lysate.

This technology may be useful because current manual processes may have certain disadvantages or limitations, such as: (a) poorer quality, (b) operator limitations, (c) work hazards, (d) ergonomics, and/or (e) safety. For example, manual dissection methods completely rely on individual operator hand/eye coordination, which may affect the consistency and accuracy of the outcome. They may also require a dedicated training plan to achieve consistent accuracy. Performing manual dissection with constant force applied to the glass surface can also cause ergonomic issues with the operator over a period of time; for example, wrist injuries such as carpal tunnel syndrome. Thus, in many laboratories, operators must also limit the number of hours they spend performing manual dissections in order to help prevent injury. In terms of safety, there is also risk of razor blade injuries from broken blades which can cause lacerations, for example. Nonetheless, a completely manual method is commonly used in current lab processes which, for instance, use a standard off-the-shelf marking pen to hand mark the area of interest from a pathologist, wherein an end user may use a razor blade or equivalent (i.e., scalpel) to scrape the area of interest on the substrate.

Automated systems for sample dissection are available; however, such systems may be costly and/or low throughput. For instance, the AVENIO® MILLISECT™ system (Roche GmbH) is a milling machine that performs automated collection of regions of interest on substrates and thus avoids the above issues with manual collection. However, the system is costly, operates slowly, and may require many systems and operators for a high volume laboratory. Thus, this system might not be suitable for high-throughput sample analyses. Laser capture dissection systems are also available from several manufacturers (e.g., Leica LMD6-7 systems). In these systems, a UV laser is used to cut through (e.g., profile or score a boundary) a ROI and an IR laser to swell an adhesive cap to remove ROI from the substrate (e.g., to improve specimen release from a substrate); the system also requires custom substrates that it can be collected for subsequent analysis.

This disclosure addresses several areas of sample dissection that may cause difficulties, and embodiments may comprise different levels of system complexity. The present systems and methods provide ways to separate a region of interest (ROI) on a substrate that may provide higher throughput, and thus faster sample dissection, while avoiding manual separation and using standard slide equipment.

The present disclosure includes, for example, systems for processing samples affixed onto a substrate including: (a) a holder unit for securing a substrate; (b) a camera positioned proximate to the holder unit; (c) a processing element configured to remove a portion of a sample affixed onto the substrate; and (d) a computing device communicatively connected to the holder unit.

According to aspects, the camera and the processing element may include: (a) an image capture engine configured to obtain a first image of a first substrate with a first affixed sample and a second image of a second substrate with a second affixed sample using the camera, (b) a digital marker engine configured to allow a user to generate a marker image that contains the first image and a digital outline of a portion of the first affixed sample, (c) an image overlay engine configured to map the overlay the marker image onto the second image such that image outlines of the first affixed sample and the second affixed sample are rotated and aligned, and (d) a sample removal engine configured to control positioning of the holder unit and the processing element so that only a portion of the second affixed sample that is within the digital outline of the first affixed sample is removed.

Accordingly, some system embodiments herein comprise a means for digitizing a mark delineating the interface between one or more ROIs on a sample (also called "S" sample herein) and other samples on the slide (denoted "X" sample herein). Such interfaces include, for example, algorithms that allow for creation of a virtual mark on a sample either by virtually tracing a previously placed manual mark on the same sample, or on a parallel sample that has been manually aligned with the sample, or by automated alignment of a parallel, previously manually marked sample to a target sample as well as virtually tracing the mark from the one sample to the other. Such means also include mechanical components needed to perform these actions.

Some system embodiments herein comprise means for separating one or more ROIs from any X sample on the slide by selectively removing via mechanical processes or ablating the X sample without impacting the ROI(s). Such means include, for example, a laser such as a pulse laser, a water jet, or a source of radio-frequency, milling, electric current, ultrasound, micro-blasting, microbead blasting, particle-blasting, sand blasting, ablating, or thermal energy that is capable of lysing or ablating animal cells. Such means also include the mechanical components needed to employ these methods and algorithms that may direct the mechanism such as a laser or water jet, for instance, specifically to the X sample while avoiding the ROI(s).

Some system embodiments herein comprise means for separating one or more ROIs from X samples by selectively chemically decomposing the X sample or cells or macromolecules therein. Such means include, for example, bleach, strong acid, strong base, or one or more enzymes selectively directed to the X sample and not to the ROI(s) on the slide as well as the mechanical components needed to employ those methods and algorithms that may direct the chemicals specifically to the X sample while avoiding the ROI(s).

In some system embodiments, the system also comprises a means for straight pass collection of one or more ROIs on a substrate. For example, straight pass may include no markings as all samples are collected. Once the X's are killed or removed, the straight pass method may be utilized as all remaining samples (e.g., only S regions) are collected. Exemplary means include, for example, particle blasting, blades such as razor blades, scalpels, curettes, scoops, punches, a vacuum source to allow for a vacuum to remove the sample, or a charged surface or medium to provide a competing surface or medium or solution (e.g., particle micro-blasting) for the ROI sample, or using adhesive medium to extract the ROI from the glass slide Such means also include other mechanical elements as needed to automatically control the use of the above elements.

In some embodiments, the system includes means for placing the ROI sample into a container. Exemplary means include, for example, mechanical components that may automatically control the process of taking ROI sample removed from a slide and putting it into or onto a container such as a well structure, a tube, or a vial.

Aspects of the present disclosure describe a method for processing samples affixed onto a substrate comprising: (a) obtaining a first image of a first substrate with a first affixed sample; (b) obtaining a second image of a second substrate with a second affixed sample; (c) generating a marker image containing the first image and a digital outline of a portion of the first affixed sample; (d) overlaying the marker image onto the second image such that image outlines of the first affixed sample and the second affixed sample are aligned; and (e) removing only a portion of the second affixed sample that is within the digital outline of the first affixed sample using a processing element.

Further aspects of the present disclosure describe a system for processing samples affixed onto a substrate, comprising: (a) a holder unit for securing a substrate; (b) a camera positioned proximate to the holder unit; (c) a processing element configured to supply a nucleic acid denaturing agent to denature nucleic acids on a portion of a sample affixed onto the substrate; and (d) a computing device communicatively connected to the holder unit.

According to aspects, the camera and the processing element may include: (a) an image capture engine configured to obtain a first image of a first substrate with a first affixed sample and a second image of a second substrate with a second affixed sample using the camera, (b) a digital marker engine configured to allow a user to generate a marker image that contains the first image and a digital outline of a portion of the first affixed sample, (c) an image overlay engine configured to overlay the marker image onto the second image such that image outlines of the first affixed sample and the second affixed sample are aligned, and (d) a nucleic acid denaturing engine configured to control positioning of the holder unit and the processing element so that only nucleic acid in the X or (RONI) portion of the second affixed sample that is within the digital outline of the first affixed sample is denatured, the nucleic acid denaturing engine comprising a chemical analyzer for performing chemical analysis, a mass spectrometer, and/or a cell analyzer for performing cell analysis.

Additional aspects describe a method for processing samples affixed onto a substrate comprising: (a) obtaining a first image of a first substrate with a first affixed sample; (b) obtaining a second image of a second substrate with a second affixed sample; (c) generating a marker image containing the first image and a digital outline of a portion of the first affixed sample; (d) overlaying the marker image onto the second image such that image outlines of the first affixed sample and the second affixed sample are aligned; and (e)

denaturing only nucleic acid in a portion of the second affixed sample that is within the digital outline of the first affixed sample using a processing element.

In another aspect, systems, methods and apparatuses for processing histological samples, e.g., FFPE slides or fixed tissues are disclosed. These systems, methods, and apparatuses overcome the limitations of the existing particle microblaster (PMB) and computer numerical control (CNC) milling technology and greatly improve ease of use and also sensitivity and/or specificity of the analytical workflow. In particular, the disclosure relates to variations in PMB and CNC milling technology, which permits efficient removal of regions of non-interest (RONI) or collecting the region of interest (ROI) from histological samples, while at the same time, minimizing loss of analytes (e.g., nucleic acids, proteins, and other macromolecules) from the ROI. The described methods are simple and can be seamlessly integrated with the downstream analytical procedures.

In accordance with the present disclosure, a combination blasting technique is used to process biological specimen mounted on substrates, e.g., glass slides. A combination of blasting material (i.e., particles) and pressurized air is force-fed into the system and directed towards the patient tissue ROI. The PMB is structured in such a way as to contain the blasted patient tissue within the walls of the PMB. Next, a vacuum is then used to take the blasted tissue from the area and accumulate it into a container. A filter may be used to partition the container to allow for vacuum build up but stops the parts from reaching the vacuum pump. This method can be used both to blast of waste region ("X") or region of interest ("S"), or all contents of interest. The blasting media can be made of different materials, including, e.g., aluminum oxide; silicon dioxide; metallic-based particles; magnetic or ferromagnetic particles; salt, ionic particles, lyophilized reagent particles.

In contrast with the existing PMB technology, which requires separation of the particles from the final target of interest (e.g., prior to downstream processing), the systems and methods of the present disclosure do not require separation of the particles from the processed sample as the particles themselves are used in the downstream process.

The instant methods also are advantageous over existing methods as it permits integration of multiple processing steps into a single step, which helps reduce cross-contamination and also allows collection of analytes such as nucleic acids from tissue specimens in a highly streamlined, efficient, and inexpensive manner. By reducing operator considerations, the presently disclosed systems and methods help reduce variability and/or increase reproducibility of histological assays such as immunohistochemistry, nuclease protection assays, etc.

Another advantage of the present technology is that the systems and/or methods of the present disclosure can be modularly applied into an existing analytical workflow, e.g., downstream analytical procedures such as microscopy, hybridization assays, sequencing, chromatography, spectrometry, ELISA, etc. This means the presently disclosed systems and/or methods can be seamlessly integrated at various pre- and post-processing steps. If desired, the systems and methods may also be applied, as a scaffold, in various downstream analytical steps.

The instant methods can be easily modified or adapted to utilize a variety of ablating particles, e.g., particles of different size, shapes, or materials can be selected based on the target tissue make and/or composition. For instance, depending on the target of interest, alternative types of materials, such as hydrophobic, polar, apolar, ion exchange capable particles, affinity specific particles, dielectric particle, lyophilized particles, etc., may be used. Also, since the reagents and systems employed herein are relatively inexpensive, the present technology can be readily integrated in an analytical workflow to significantly improve performance without overtly raising the cost of the assay.

The present disclosure therefore relates, in part, to the following non-limiting embodiments:

In some embodiments, the disclosure relates to a method of processing a biological sample for a biological assay, comprising (a) contacting the biological sample with a contact medium comprising a particulate substance and pressurized air under conditions sufficient to effectuate at least partial transfer of a component in the biological sample to the contact medium; and (b) removing the contact medium from the biological sample. Preferably, the biological sample is processed for analysis of one or more analytes of diagnostic interest.

The disclosure relates to a method of processing a biological sample for a biological assay according to the foregoing or following embodiments, e.g., for the analysis of one or more analytes of diagnostic interest, wherein the biological sample comprises punch biopsy specimens, needle biopsy specimens, fresh tissues, tissue cultures, frozen tissue specimen, neutral formalin-treated tissues, organs, organelles, formalin fixed paraffin embedded (FFPE) tissues, wax-fixed embedded tissues, ethanol-fixed paraffin-embedded (EFPE) tissues, hematoxylin and eosin (H&E) stained tissues, or glutaraldehyde fixed tissues. Preferably, the biological sample comprises FFPE or EFPE tissues. Preferably, the biological sample contains cells from tumor tissue, degenerative tissues, inflamed tissues (e.g., tissue from a patient suffering from an inflammatory disease such as rheumatoid arthritis, ulcerative colitis, Crohn's disease, etc.

The disclosure relates to a sample milling device that includes a first and a second component. The first component has openings on both ends. The second component is secured to one end of the first component and has a sample collection opening facing away from where the second component is secured to the first component. The sample collection opening has one or more sample scraping elements that protrude along a perimeter of the sample collection opening. A vacuum channel extends through the first and second components to connect the sample collection opening with a vacuum connection opening on the other end of the first component.

The disclosure relates to a method of processing a biological sample for a biological assay according to the foregoing or following embodiments, e.g., for the analysis of one or more analytes of diagnostic interest, comprising contacting a region of interest (ROI), a region of non-interest (RONI), or all regions in the biological sample with the contact medium; preferably contacting a region of interest (ROI) with the contact medium.

The disclosure relates to a method of processing a biological sample for a biological assay according to the foregoing or following embodiments, e.g., for the analysis of one or more analytes of diagnostic interest, wherein the biological sample comprises at least one analyte of diagnostic interest selected from genomic DNA (gDNA), methylated DNA, specific methylated DNA, messenger RNA (mRNA), fragmented DNA, fragmented RNA, fragmented mRNA, mitochondrial DNA (mtDNA), chloroplast DNA (ctDNA), viral RNA or viral DNA, microRNA, ribosomal RNA, in situ PCR product, polyA mRNA, RNA/DNA hybrid, lipid, carbohydrate, protein, glycoprotein, lipoprotein, phosphoprotein, specific phosphorylated or acetylated variant of a protein, or viral coat proteins; preferably nucleic acids selected from mRNA, gDNA, viral DNA or viral RNA.

The disclosure relates to a method of processing a biological sample for a biological assay according to the foregoing or following embodiments, e.g., for the analysis of one or more analytes of diagnostic interest, wherein the particulate substance in the blast medium comprises aluminum oxide; silicon dioxide; metallic-based particles; magnetic or ferromagnetic particles or a combination thereof.

The disclosure relates to a method of processing a biological sample for a biological assay according to the foregoing or following embodiments, e.g., for the analysis of one or more analytes of diagnostic interest, wherein the particulate substance is capable of binding to an analyte or a non-analyte in the biological sample; preferably, the particulate substance is capable of binding to the analyte via an interaction selected from ionic interaction, polar-apolar interaction, hydrophobic interaction, van der waal's interaction, chemical coupling, dielectric or zwitterion interaction or a combination thereof.

The disclosure relates to a method of processing a biological sample for a biological assay according to the foregoing or following embodiments, e.g., for the analysis of one or more analytes of diagnostic interest, wherein the contact medium comprises pressurized air selected from pressurized helium, argon, xenon, nitrogen, carbon dioxide, or a combination thereof.

The disclosure relates to a method of processing a biological sample for a biological assay according to the foregoing or following embodiments, e.g., for the analysis of one or more analytes of diagnostic interest, wherein the biological sample is mounted on a substrate, e.g., a substrate is selected from glass, silicon, poly-L-lysine coated material, nitrocellulose, polystyrene, cyclic olefin copolymers (COCs), cyclic olefin polymers (COPs), polypropylene, polyethylene, paper and/or polycarbonate.

The disclosure relates to a method of processing a biological sample for a biological assay according to the foregoing or following embodiments, e.g., for the analysis of one or more analytes of diagnostic interest, wherein the biological sample comprises a nucleic acid analyte and the contact medium comprises a particulate substance comprising silica.

The disclosure relates to a method of processing a biological sample for a biological assay according to the foregoing or following embodiments, e.g., for the analysis of one or more analytes of diagnostic interest, further comprising micro-dissection, e.g., laser micro-dissection.

The disclosure relates to a method of processing a biological sample for a biological assay according to the foregoing or following embodiments, e.g., for the analysis of one or more analytes of diagnostic interest, wherein the contact medium is removed from the biological sample via vacuuming, pressure differential or gradient, gravity, a transport medium (e.g., liquid or aerosol or gas), or a transfer medium selected from magnetic field or electric field.

The disclosure relates to a method of processing a biological sample for a biological assay according to the foregoing or following embodiments, e.g., for the analysis of one or more analytes of diagnostic interest, comprising (a) selectively contacting a region of non-interest (RONI) in the biological sample with the contact medium, wherein the selective contacting preferably comprises leaving a region of interest (ROI) in the biological sample untouched; (b) selectively contacting a region of interest (ROI) in the biological sample with the contact medium, wherein the selective contacting preferably comprises leaving a region of non-interest (RONI) in the biological sample untouched; or (c) contacting both ROI and RONI in the biological sample with the contact medium.

The disclosure relates to a method of processing a biological sample for a biological assay according to the foregoing or following embodiments, e.g., for the analysis of one or more analytes of diagnostic interest, comprising collecting the particulate substance in the contact medium; (c) optionally preparing the particulate substance for analysis; and (d) further optionally analyzing the particulate substance.

The disclosure relates to a method of processing a biological sample for a biological assay according to the foregoing or following embodiments, e.g., for the analysis of one or more analytes of diagnostic interest, wherein the preparing the particulate substance for analysis comprises treating the particulate substance with a buffer (e.g., lysis buffer) and washing the particulate substance to remove non-analytes. Preferably under this embodiment, the analysis of particulate substance comprises polymerase chain reaction (PCR), quantitative PCR (qPCR), reverse transcriptase PCR (RT-PCR), nucleic acid sequence based amplification (NASBA), loop mediated isothermal amplification (LAMP), rolling circle amplification (RCA), immunoassay, immunoPCR (iPCR), enzyme activity assay, staining, imaging, whole genome amplification (WGA), in situ PCR, in situ WGA, polony formation, sequencing, single-molecule sequencing, nanopore analysis, nanopore sequencing, single-molecule imaging, DNA ball formation, electrophoresis, microelectromechanical systems (MEMS) electrophoresis, mass spectrometry, chromatography (e.g., HPLC), proximity ligation assay, electrochemical detection, plasmon resonance (SPR), hybridization assay (e.g., in situ hybridization assay such as fluorescence in situ hybridization (FISH)) FRET, cell sorting (e.g., FACS), electrochemiluminescence ELISA, and chemiluminescence ELISA.

The disclosure relates to a method of processing a biological sample for a biological assay according to the foregoing or following embodiments, e.g., for the analysis of one or more analytes of diagnostic interest, wherein the method further comprises mixing the contact medium with an enriching medium. Preferably under this embodiment, the enriching medium comprises a substance which binds specifically to an analyte of interest in the biological sample, e.g., an antibody which specifically binds to a protein antigen of interest or a nucleic acid which specifically hybridizes to a nucleic acid of interest.

The disclosure relates to a method of processing a biological sample for a biological assay according to the foregoing or following embodiments, e.g., for the analysis of one or more analytes of diagnostic interest, wherein the biological sample comprises a two-dimensional tissue (e.g., tissue section or slice) or a three-dimensional tissue (e.g., tissue block) comprising a well-defined spatial location of a region of interest (ROI) and/or a region of non-interest (RONI); preferably both ROI and RONI.

In some embodiments, the disclosure relates to a method of assaying for an analyte in a biological sample comprising processing the biological sample by (a) contacting the biological sample with a contact medium comprising a particulate substance and pressurized air under conditions sufficient to effectuate at least partial transfer of a component in the biological sample to the contact medium; and (b) removing the contact medium from the biological sample to obtain a processed biological sample; and assaying for the analyte in the processed biological sample or the removed contact medium.

In some embodiments, the disclosure relates to a bioanalytical system comprising (a) a first component for contacting a biological sample or a region therein with a contact medium comprising a particulate substance and pressurized air under conditions sufficient to effectuate at least a partial transfer of a component in the biological sample to the contact medium; (b) a second component for removing the contact medium from the biological sample; and (c) optionally a third component for analyzing the component in the contact medium or the processed biological sample or both the contact medium and the processed biological sample.

The disclosure relates to a bioanalytical system of the foregoing or the following embodiments, wherein the first component comprises a pressurized particle micro-blaster (PMB) containing the contact medium.

The disclosure relates to a bioanalytical system of the foregoing or the following embodiments, wherein the second component comprises a vacuum, pressure differential or gradient, a medium for transporting the particulate substance (e.g., liquid or aerosol), or a transfer medium selected from magnetic field or electric field.

The disclosure relates to a bioanalytical system of the foregoing or the following embodiments, wherein the optional third component comprises an instrument selected from polymerase chain reaction (PCR), quantitative PCR (qPCR), reverse transcriptase PCR (RT-PCR), nucleic acid sequence based amplification (NASBA), loop mediated isothermal amplification (LAMP), rolling circle amplification (RCA), immunoassay, immunoPCR (iPCR), enzyme activity assay, staining, imaging, whole genome amplification (WGA), in situ PCR, in situ WGA, polony formation, sequencing, single-molecule sequencing, nanopore analysis, nanopore sequencing, single-molecule imaging, DNA ball formation, electrophoresis, microelectromechanical systems (MEMS) electrophoresis, mass spectrometry, chromatography (e.g., HPLC), proximity ligation assay, electrochemical detection, plasmon resonance (SPR), hybridization assay (e.g., in situ hybridization assay such as fluorescence in situ hybridization (FISH)) FRET, cell sorting (e.g., FACS), electrochemiluminescence ELISA, and chemiluminescence ELISA.

Some embodiments presented in this disclosure concern an Automated Tissue Dissection (ATD) System. An ATD system is a one stop, and potentially low-cost, system to perform dissections on a substrate from pathologist digital mark or pen mark on the substrate using non-contact and/or mechanical method to extract a Formalin-Fixed Paraffin-Embedded (FFPE) tissue sample with: (a) only the ROI or ROIs as area to be saved; and (b) remove or decompose DNA in the region of no interest (RONI) and collect all tissue sample from a standard microscope substrate into a specific container.

BRIEF DESCRIPTION OF THE DRAWINGS

FIG. 8A shows representative implementation of PMB of the disclosure to process patient samples; and FIG. 8B shows representative implementation of PMB of the disclosure to process patient samples.

DETAILED DESCRIPTION

Definitions

Figure 1:
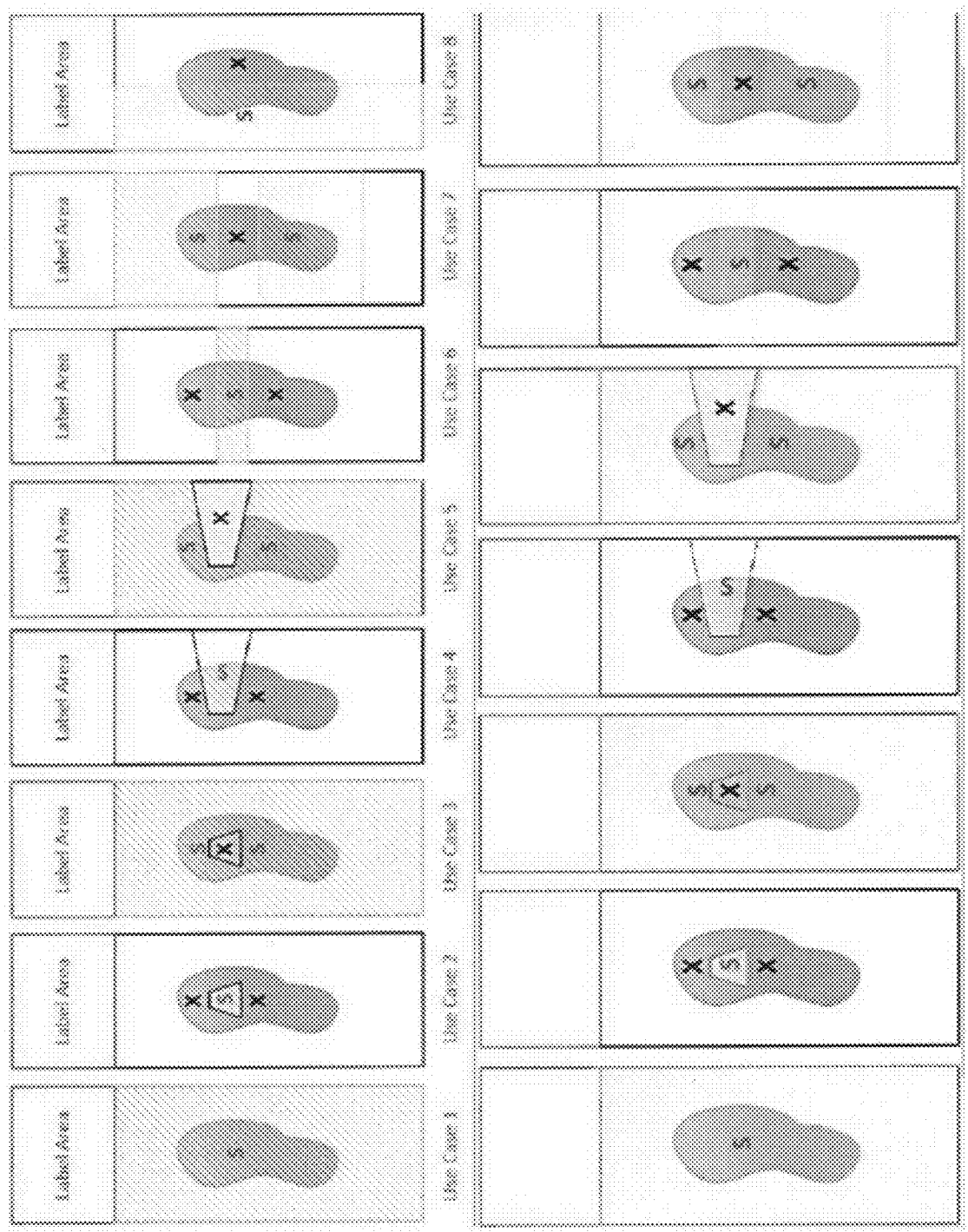
FIG. 1 shows schematic representations of various scrapping methods that are utilized in accordance with various embodiments.

Some of the terms used herein are defined as described in this section. Other terms are defined or exemplified elsewhere in the disclosure. Unless defined otherwise, technical and scientific terms used herein have the same meaning as commonly understood by one of ordinary skill in the art to which this invention belongs.

In this application, the use of "or" means "and/or" unless stated otherwise. In the context of a multiple dependent claim, the use of "or" refers back to more than one preceding independent or dependent claim in the alternative only.

The word "about" means a range of plus or minus 10% of that value, e.g., "about 5" means 4.5 to 5.5, "about 100" means 90 to 100, etc., unless the context of the disclosure indicates otherwise, or is inconsistent with such an interpretation. For example in a list of numerical values such as "about 49, about 50, about 55", "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

Where a range of values is provided in this disclosure, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also disclosed.

As used herein, the term "plurality" can be 2, 3, 4, 5, 6, 7, 8, 9, 10, or more.

As used herein, the term "detecting," refers to the process of determining a value or set of values associated with a sample by measurement of one or more parameters in a sample, and may further comprise comparing a test sample against reference sample. In accordance with the present disclosure, the detection of tumors includes identification, assaying, measuring and/or quantifying one or more markers.

The term "likelihood," as used herein, generally refers to a probability, a relative probability, a presence or an absence, or a degree.

As used herein, the terms "comprise" (or variations thereof), "contain" (or variations thereof), "have" (or variations thereof), or "include" (or variations thereof), are not intended to be limiting, are inclusive or open-ended and do not exclude additional, unrecited additives, components, integers, elements or method steps. For example, a process, method, system, composition, kit, or apparatus that comprises a list of features is not necessarily limited only to those features but may include other features not expressly listed or inherent to such process, method, system, composition, kit, or apparatus.

The term "sample" as used herein refers to a composition that is obtained or derived from a subject of interest that contains a cellular and/or other molecular entity that is to be characterized and/or identified, for example based on physical, biochemical, chemical and/or physiological characteristics. Preferably, the sample is a "biological sample," which means a sample that is derived from a living entity, e.g., cells, tissues, organs and the like. In some embodiments, the source of the tissue sample may be blood or any blood constituents; bodily fluids; solid tissue as from a fresh, frozen and/or preserved organ or tissue sample or biopsy or aspirate; and cells from any time in gestation or development of the subject or plasma. Samples include, but not limited to, primary or cultured cells or cell lines, cell supernatants, cell lysates, platelets, serum, plasma, fluids (e.g., lymph, amniotic, milk, whole blood, urine, CSF, saliva, sputum, tears, perspiration, mucus, tumor lysates, and cell culture medium), homogenized tissue, tumor tissue, and cellular extracts. Samples further include biological samples that have been manipulated, e.g., via treatment with reagents, solubilized, or enriched for certain components, such as proteins or nucleic acids, or embedded in a semi-solid or solid matrix for sectioning purposes, e.g., a thin slice of tissue or cells in a histological sample. Samples may contain environmental components, such as, e.g., water, soil, mud, air, resins, minerals, etc. Preferably, the biological sample contains DNA (e.g., gDNA, mtDNA), RNA (e.g., mRNA, tRNA), protein, or combinations thereof, obtained from a subject (e.g., human or other mammalian subject).

As used herein, the term "cell" is used interchangeably with the term "biological cell." Non-limiting examples of biological cells include eukaryotic cells, plant cells, animal cells, such as mammalian cells, reptilian cells, avian cells, fish cells, or the like, prokaryotic cells, bacterial cells, fungal cells, protozoan cells, or the like, cells dissociated from a tissue, such as muscle, cartilage, fat, skin, liver, lung, neural tissue, and the like, immunological cells, such as T cells, B cells, natural killer cells, macrophages, and the like, embryos (e.g., zygotes), oocytes, ova, sperm cells, hybridomas, cultured cells, cells from a cell line, cancer cells, infected cells, transfected and/or transformed cells, reporter cells, and the like. A mammalian cell can be, for example, from a human, a mouse, a rat, a horse, a goat, a sheep, a cow, a primate, or the like.

As used herein, the term "tumor" includes any cell or tissue that may have undergone transformation at the genetic, cellular, or physiological level compared to a normal or wild-type cell. The term usually denotes neoplastic growth which may be benign (e.g., a tumor which does not form metastases and destroy adjacent normal tissue) or malignant/cancer (e.g., a tumor that invades surrounding tissues, and is usually capable of producing metastases, may recur after attempted removal, and is likely to cause death of the host unless adequately treated). See Steadman's Medical Dictionary, $28^{th}$ Ed Williams & Wilkins, Baltimore, Md. (2005).

The term "cancer" refers to abnormal cell growth, particularly cancers and carcinomas, sarcomas, adenocarcinomas, lymphomas, leukemia, solid and lymphoid cancers, etc. which are malignant in nature. Examples of different types of cancer include, but are not limited to, lung cancer, pancreatic cancer, breast cancer, gastric cancer, bladder cancer, oral cancer, ovarian cancer, thyroid cancer, prostate cancer, uterine cancer, testicular cancer, neuroblastoma, squamous cell carcinoma of the head, neck, cervix and vagina, multiple myeloma, soft tissue and osteogenic sarcoma, colorectal cancer, liver cancer, renal cancer (e.g., RCC), pleural cancer, cervical cancer, anal cancer, bile duct cancer, gastrointestinal carcinoid tumors, esophageal cancer, gall bladder cancer, small intestine cancer, cancer of the central nervous system, skin cancer, choriocarcinoma; osteogenic sarcoma, fibrosarcoma, glioma, melanoma, etc.

The term "normal" as used in the context of "normal cell," is meant to refer to a cell of an untransformed phenotype or exhibiting a morphology of a non-transformed cell of the tissue type being examined (e.g., PBMC). In some embodiments, "normal sample" as used herein includes non-tumor sample, e.g., saliva sample, skin sample, hair sample or the like. It should be noted that the methods of the disclosure may be implemented without the use of normal samples.

The term "abnormal," as used herein, generally refers to a state of a biological system that deviates in some degree from normal (e.g., wild-type). Abnormal states can occur at the physiological or molecular level. Representative examples include, e.g., physiological state (disease, pathology) or a genetic aberration (mutation, single nucleotide variant, copy number variant, gene fusion, indel, etc.). A disease state can be cancer or pre-cancer. An abnormal biological state may be associated with a degree of abnormality (e.g., a quantitative measure indicating a distance away from normal state).

As used herein, the term "marker" refers to a characteristic that can be objectively measured as an indicator of normal biological processes, pathogenic processes or a pharmacological response to a therapeutic intervention, e.g., treatment with an anti-cancer agent. Representative types of markers include, for example, molecular changes in the structure (e.g., sequence) or number of the marker, comprising, e.g., gene mutations, gene duplications, amino acid substitutions, additions, or deletions, or a plurality of differences, such as somatic alterations in DNA, copy number variations, tandem repeats, translocations or a combination thereof.

As used herein, the term "genetic marker" refers to a sequence of polynucleotide that has a specific location on a genome or corresponds to the specific location in the genome (e.g., a transcript which is complementary to the sequence of the genomic location). Thus, term "genetic marker" can also be used to refer to, e.g., a cDNA and/or an mRNA encoded by a genomic sequence, as well as to that genomic sequence itself. Genetic markers may include two or more alleles or variants. Genetic markers include nucleic acid sequences which either do or do not code for a gene product (e.g., a protein). Particularly, the genetic markers include single nucleotide polymorphisms/variations or copy number variations or a combination thereof. Preferably, the genetic marker includes somatic variations in the DNA, e.g., sSNV or sCNV, indels, SVs, or a combination thereof compared to a reference sample.

As used herein, the term "protein marker" or "proteomic marker" refers to a sequence of polypeptide or a fragment thereof, e.g., a biologically active fragment of a polypeptide, that corresponds to a transcript (e.g., is encoded by a transcript), which in turn may correspond to a genomic sequence (e.g., a transcript which is transcribed by a DNA sequence).

A "formalin-fixed, wax-embedded" or a "formalin-fixed, paraffin-embedded" or "FFPE" tissue sample herein is broadly construed to refer to a sample that has been fixed with formalin or an equivalent substance and embedded in wax, such as paraffin wax or an equivalent substance. FFPE tissue herein may from any human, animal or plant source.

A "slide" herein may be any type of surface capable of holding FFPE tissue for analysis and may be made out of any suitable materials.

A "region of interest" or "ROI" herein refers to a portion of a sample on a substrate that a user may wish to analyze, such as to evaluate alterations in the sequence, structure, or expression level of genes. Samples on a substrate may be comprised of all ROI, no ROI, one ROI, or more than one ROI. An ROI is also referred to as "S" sample herein. A RONI sample on a substrate is referred to herein as "X" sample.

As used herein, the term "particulate" substance means a substance comprised of particles, such as substantially spherical particles or less irregularly shaped particles. Typically, the particulate substances have a diameter of about 10 nm to about 100 μm; preferably from about 50 to about 400 nm; especially from about 100 to about 200 nm.

As used herein, the term "assay" is a test or testing for the quantity, presence, or absence of a substance.

As used herein, the term "pressurized" air means air that has been compressed, e.g., with pressure that is greater than atmospheric pressure. The "air" component in such pressurized is typically an inert gas selected from helium, argon, xenon, nitrogen, carbon dioxide, or a mixture thereof. As is typical in pressurized systems, the "air" component may be in liquid, semi-liquid, or gaseous form.

As used herein, "contacting" means that the composition comprising an agent (e.g. contact medium) is introduced into a sample containing a target, e.g., cell target, in a test tube, flask, tissue culture, chip, array, plate, microplate, capillary, or the like, and incubated at a temperature and time sufficient to permit an interaction between the target and the agent.

In the in vivo diagnostic or therapeutic context, "contacting" means that an active ingredient (e.g., a chemical compound or a drug) is introduced into a subject, and the active ingredient is allowed to come in contact with the subject's target tissue, e.g., epithelial tissue, in vivo.

As used herein, the term "subject" means any animal, preferably a mammal such as a human, a veterinary or farm animal, a domestic animal or pet, including animals normally used for clinical research. Particularly, the subject is a human subject, e.g., a human patient diagnosed with disease such as cancer. A subject may have, potentially have, or be suspected of having one or more characteristics associated with a disease, a symptom(s) associated with the disease, asymptomatic with respect to the disease or undiagnosed. Particularly, the subject may have cancer, the subject may show a symptom(s) associated with cancer, the subject may be free from symptoms associated with cancer, or the subject may not be diagnosed with cancer.

As used herein, the term "noise" in its broadest sense refers to any undesired disturbances (e.g., signal not directly associated with the true event) which may nonetheless be processed or received as true events. Noise is the summation of unwanted or disturbing energy introduced into a system from man-made and natural sources. Noise may distort a signal such that the information carried by the signal becomes degraded or less reliable. The term is contrasted with "signal," which is a function that conveys information about the behavior or attributes of some phenomenon, e.g., probabilistic association between a marker (SNV, CNV, indel, SV) and a disease such as cancer.

As used herein, the term "estimate" in the context of marker levels is used in a broad sense. As such, the term "estimate" may refer to an actual value (e.g., 1 variation per mbp DNA), a range of values, a statistical value (e.g., mean, median, etc.) or other means of estimation (e.g., probabilistically).

As used herein, the term "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

As used herein, the term "component" refers to constituent of a system. For example, in a cell system, components may include polypeptides (e.g., small peptides as well as large proteins), nucleic acids (e.g., DNA or RNA), carbohydrates (e.g., simple sugars as well as macromolecules such as starch), lipids, and other constituents such as vitamins and cholesterol.

As used herein, the term "transfer" is used in the broadest sense to refer to a movement of a component of a system from its natural environment (e.g., mitochondria in the case of mitochondrial DNA) to an unnatural environment (e.g., surface of silica particle) via a process such as binding, bonding, adsorption, etc. The term includes processes such as covalent or non-covalent interactions between the component and the unnatural system.

As used herein, the term "covalent" interaction involve sharing of electrons between the bonded atoms. In contrast, "non-covalent" interactions may include, for example, ionic interactions, electrostatic interactions, hydrogen bonding interactions, physiochemical interactions, van der Waal forces, Lewis-acid/Lewis-base interactions, or combinations thereof.

As used herein, the term "analyte" generally refers to a target molecule(s) that is detected using the methods or systems disclosed herein. The analyte can be a DNA analyte, an RNA analyte, a nucleic acid analyte, macromolecule or a small molecule as those terms are used in the art. In particular, a macromolecule may include, for example, a polynucleotide, a polypeptide, a carbohydrate, a lipid, or a combination of one or more of these. As a general rule, the molecular mass of a macromolecule is at least about 300 Daltons and can be millions of Daltons. A small molecule is an organic compound having a molecular weight of up to about 300 Daltons. In certain instances, the analyte is a nucleic acid analyte.

As used herein, a "probe" is a substance, e.g., a molecule, which can recognize or be specifically recognized by a particular target. The types of potential probe/target or target/probe binding partners include receptor/ligand; ligand/antiligand; nucleic acid (polynucleotide) interactions, including DNA/DNA, DNA/RNA, PNA (peptide nucleic acid)/nucleic acid; enzymes, other catalysts, or other substances, with substrates, small molecules or effector molecules; etc. Examples of probes that are contemplated by this invention include, but are not limited to, peptides, enzymes (such as proteases or kinases), enzyme substrates, cofactors, drugs, lectins, sugars, nucleic acids (including oligonucleotides, DNA, RNA, PNA or modified or substituted nucleic acids), oligosaccharides, proteins, enzymes, polyclonal and monoclonal antibodies, single chain antibodies, or fragments thereof. Probe polymers can be linear or cyclic. Probes can distinguish between different targets, either by virtue of differential activity, differential binding or through identification from structural markers. The probes of the invention are preferably nucleic acid molecules, particularly preferably DNA. In certain instances "probes" may function as "targets" and "targets" may function as probes, e.g., a complementary DNA (cDNA) may serve as a probe that hybridizes to a portion of a target gene sequence; however, the cDNA itself corresponds to the target sequence since it matches with the mRNA product of the gene sequence.

As used herein, the term "analysis" as well as the phrase "detection" may refer to qualitative or quantitative determination of a parameter of interest concerning the analyte, e.g., amount, level, concentration, or activity of the analyte (both absolute and relative).

As used herein, the term "diagnosis" refers to methods by which a determination can be made as to whether a subject is likely to be suffering from a given disease or condition. The skilled artisan often makes a diagnosis on the basis of one or more diagnostic indicators, e.g., a marker, the presence, absence, amount, or change in amount of which is indicative of the presence, severity, or absence of the disease or condition. Other diagnostic indicators can include patient history; physical symptoms, e.g., unexplained weight loss, fever, fatigue, pains, or skin anomalies; phenotype; genotype; or environmental or heredity factors. A skilled artisan will understand that the term "diagnosis" refers to an increased probability that certain course or outcome will occur; that is, that a course or outcome is more likely to occur in a patient exhibiting a given characteristic, e.g., the presence or level of a diagnostic indicator, when compared to individuals not exhibiting the characteristic. Diagnostic methods of the disclosure can be used independently, or in combination with other diagnosing methods, to determine whether a course or outcome is more likely to occur in a patient exhibiting a given characteristic.

The term "nucleic acid" generally refers to DNA or RNA, whether it is a product of amplification, synthetically created, products of reverse transcription of RNA or naturally occurring. Typically, nucleic acids are single- or double-stranded molecules and are composed of naturally occurring nucleotides. Double-stranded nucleic acid molecules can have 3' or 5' overhangs and as such are not required or assumed to be completely double-stranded over their entire length. Furthermore, the term nucleic acid can be composed of non-naturally occurring nucleotides and/or modifications to naturally occurring nucleotides. Examples are listed herein, but are not limited to: phosphorylation of 5' or 3' nucleotides to allow for ligation or prevention of exonuclease degradation/polymerase extension, respectively; amino, thiol, alkyne, or biotinyl modifications for covalent and near covalent attachments; fluorophores and quenchers; phosphorothioate, methylphosphonates, phosphoroamidates and phosphorotiester linkages between nucleotides to prevent degradation; methylation; and modified bases.

The term "polypeptide" when used herein means a peptide, a protein, or a polypeptide which are used interchangeable and which encompasses amino acid chains of a given length, wherein the amino acid residues are linked by covalent peptide bonds. The term polypeptide also refers to, and does not exclude, modifications of the polypeptide. Modifications include glycosylation, acetylation, acylation, phosphorylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

As used herein, the term "isolated" or "extracted" in the context of a molecule refers to a molecule that is substantially free of impurities. A molecule (such as, DNA or RNA) has been "isolated" or "extracted" when it is purified away from other components in a sample. Purification refers to separating the target from one or more extraneous components also found in a sample. Components that are isolated, extracted or purified from a mixed specimen or sample typically are purified or enriched by at least 50%, at least 60%, at least 75%, at least 90%, or at least 98% or even at least 99% compared to the unpurified or non-extracted sample.

The term "synthetic" refers to molecules that have been chemically synthesized using art-understood techniques, e.g., using phosphoramidite chemistry or synthetic chemistry.

The term "hybrid" or "hybridize" in the context of a nucleic acid is broadly meant to include duplexes as well as molecules that are capable of such forming duplexes. In this context, single-stranded nucleic acids that base pair over a number of bases are said to "hybridize." Hybridization is typically determined under physiological or biological conditions (e.g., intracellular: pH 7.2, 140 mM potassium ion; extracellular: pH 7.4, 145 mM sodium ion).

As used herein, the term "analog" includes, but is not limited to, oligonucleotides having residues or linkers synthetically introduced therein, such as a ribonucleic acid residue within a DNA sequence, a branching linking agent such as a glycerol derivative, or an aminoalkyl linker, for example. "Adducts" include, for example, 06-alkyl-dG and O6-Me-dG Likewise, the term "conjugate" in one embodiment, refers to a target recognition agent covalently or non-covalently bound to one or more polynucleotides. In another embodiment, term "conjugate" refers to a linear, branched, or dendritic polynucleotide covalently or non-covalently to one or more fluorescent dye molecules.

As used herein, "target" refers to a substance whose presence, activity and/or amount is desired to be determined and which has an affinity for a given probe. Targets can be man-made or naturally-occurring substances. Also, they can be employed in their unaltered state or as aggregates with other species. Targets can be attached, covalently or non-covalently, to a binding member, either directly or via a specific binding substance. Examples of targets which can be employed in this invention include, but are not limited to, nucleic acids or polynucleotides (including mRNA, tRNA, rRNA, oligonucleotides, DNA, viral RNA or DNA, ESTs, cDNA, PCR-amplified products derived from RNA or DNA, and mutations, variants or modifications thereof); proteins (including enzymes, such as those responsible for cleaving neurotransmitters, proteases, kinases and the like); substrates for enzymes; peptides; cofactors; lectins; sugars; polysaccharides; cells (which can include cell surface antigens); cellular membranes; organelles; etc., as well as other such molecules or other substances which can exist in complexed, covalently bonded crosslinked, etc. form. Targets can also be referred to as anti-probes.

Wherein the probe binds to a target sequence, the binding may be "specific" or "selective." In general, if a probe has one and only one binding partner (e.g., target), it possesses the property of "specificity." In practicality, the vast majority of probes are "selective" rather than "specific" because most probes will bind to a number of targets, particularly at high concentrations. Thus, the terms are used interchangeably. Specificity and selectivity of binding can be determined using routine methods. For instance, wherein the target is a particular mRNA, the probe can be, e.g., an oligonucleotide, which binds specifically to the target but not to interfering RNAs or DNAs, under selected hybridization conditions. One of skill in the art can, using art-recognized methods, determine experimentally the features of an oligonucleotide that will hybridize optimally to the target, with minimal hybridization to non-specific, interfering DNA or RNA (e.g., see above). In general, the length of an oligonucleotide probe used to distinguish a target mRNA present in a background of a large excess of untargeted RNAs can range from about 8 to about 50 nucleotides in length, preferably about 18, 20, 22 or 25 nucleotides. An oligonucleotide probe for use in a biochemical assay in which there is not a large background of competing targets can be shorter than 8 nucleotides. Using art-recognized procedures (e.g., the computer program BLAST), the sequences of oligonucleotide probes can be selected such that they are mutually unrelated and are dissimilar from potentially interfering sequences in known genetics databases. The selection of hybridization conditions that will allow specific hybridization of an oligonucleotide probe to the RNA target can be determined routinely, using art-recognized procedures.

As used herein, the term "primer" refers to short nucleic acid molecules, such as DNA oligonucleotides comprising nine or more nucleotides, which in some examples is used to initiate the synthesis of a longer nucleic acid sequence. Longer primers can be about 10, 12, 15, 20, 25, 30 or 50 nucleotides or more in length. Primers may also be used in detection.

"Mechanically removing or ablating" certain samples from a substrate herein means either separating that sample from the substrate or vaporizing or otherwise decomposing the sample by mechanical means so that it is no longer present on the substrate.

To "decompose" macromolecules chemically herein means to denature or break down macromolecules such as RNA, DNA, and/or proteins or to chemically modify them sufficiently that they will not contaminate a later analysis of RNA, DNA, and/or proteins in ROI tissue.

A "mark" made on a slide by a pathologist or laboratory user or other individual is referred to herein as a "manual mark." Such a mark may be made by any available means, such as with a pen or etching equipment. A mark that is made automatically by a system herein, in contrast, may be termed a "virtual mark" or a "digital mark" to indicate that it is not made manually but by the use of one or more algorithms.

The terms "digital," "digitized," "automated," and "automatically" and the like indicate actions that are performed by a system herein, for example, controlled by algorithms and/or by interaction between a user and a computer user interface as opposed to actions that are performed manually by a user.

As used herein, the term "surface" refers to any matter that provides a site which permits interaction between an analyte or a probe of interest. Preferably, the surface is a surface of a solid support, e.g., nitrocellulose, the walls of wells of a reaction tray, multi-well plates, test tubes, polystyrene beads, magnetic beads, membranes, and microparticles (such as latex particles). Any suitable porous material with sufficient porosity to allow access by detector reagents and a suitable surface affinity to immobilize capture reagents (e.g., oligonucleotides) is contemplated by this term. For example, the porous structure of nitrocellulose has excellent absorption and adsorption qualities for a wide variety of reagents, for instance, capture reagents. Nylon possesses similar characteristics and is also suitable. Microporous structures are useful, as are materials with gel structure in the hydrated state. Further examples of useful solid supports include natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer.

As used herein, the term "signature" refers to a collection of markers which indicate a phenotype of interest, e.g., a cancer signature comprising ≥3 mutations which indicates that the cell or tissue harboring the mutations is a tumor cell. In some embodiments, a signature comprises the presence, absence, and/or abundance of a combination of the markers, e.g., tumor markers. By combining the various probe sets, a reliable method for the detection of a phenotype of interest can be designed. Such a signature test that is conducted as a single assay can provide great benefit for assessing and understanding the interplay between the various markers.

The term "amplification" generally refers to the production of a plurality of nucleic acid molecules from a target nucleic acid wherein primers hybridize to specific sites on the target nucleic acid molecules in order to provide an initiation site for extension by a polymerase. Amplification can be carried out by any method generally known in the art, such as but not limited to, standard PCR, long PCR, hot start PCR, qPCR, RT-PCR and real time PCR.

The term "antibody" as used herein refers to a complete immunoglobulin, such as an IgA, IgD, IgE, IgG or IgM or to a fragment of an antibody (especially an antigen-binding fragment), such as a Fab, Fv or Fc or a fused antibody, a fused antibody fragment or any other derivative of an antibody. The term "labeled antibody" refers to an antibody that is labeled with an enzyme, a fluorescent dye, a chemiluminescent substance, biotin, avidin or a radioisotope.

The term "epitope" refers to an antigenic region of a compound, such as a protein, a carbohydrate or a lipid. The antigenic region typically consists of 5 to 8 amino acids. The epitope is specifically recognized by the antigen binding sites of the respective antibody.

The term "fixed tissue or cell" is used herein as known to the expert skilled in the art and refers to biological tissue or cells which are preserved from decay by chemical fixation methods. Such methods prevent autolysis or putrefaction within such biological tissue or cells. Fixation terminates biochemical reactions and increases the mechanical stability of the treated tissue.

The term "immuno-histochemistry" or "IHC" refers to a technique for detecting the presence of an antigen with an antibody capable of specifically binding to said antigen in histological samples. The detection of the antibody-antigen complex occurs usually by a chromogenic reaction with an enzyme-labeled antibody or by a fluorescent labeled antibody.

The term "macrodissection" as used herein refers to the process of scratching an area of interest from a tissue section mounted on a solid support, such as a microscope slide, by using a tool such as a scalpel or a spatula. The term "microdissection" as used herein refers to the process of cutting and separating one or more specific cells or an area of interest from a tissue sample. Microdissection can for example be performed using laser capture microdissection (LCM) by cutting the relevant area with a laser.

The term "membrane slide" as used herein refers to solid supports or microscope slides for use in Laser Capture Microdissection (LCM). For microdissection glass slides covered with a membrane or frame slides that consist of a metal frame which can be covered with various membranes can be used.

The term "poly-lysine" refers to a molecule that contains up to several hundreds of repeating units and is suitable for increasing the affinity between a sample, such as a tissue section, and the membrane side onto which the sample is mounted. A poly-lysine according to the description is poly-L-lysine. Poly-L-lysine according to the description has a molecular weight from 70 to 300 kDa. Poly-L-lysine can be digested by proteases. Another poly-lysine according to the description is for example poly-D-lysine. Poly-D-lysine according to the description has a molecular weight from 70 to 300 kDa. Poly-D-lysine is resistant to protease digestion.

The term "qPCR" generally refers to the PCR technique known as real-time quantitative polymerase chain reaction, quantitative polymerase chain reaction or kinetic polymerase chain reaction. This technique simultaneously amplifies and quantifies target nucleic acids using PCR wherein the quantification is by virtue of an intercalating fluorescent dye or sequence-specific probes which contain fluorescent reporter molecules that are only detectable once hybridized to a target nucleic acid.

The term "RNA" is used herein as known to the expert skilled in the art and refers to pre-mRNA, pre-mRNA transcripts, mRNA, transcript processing intermediates, mature mRNA used for translation and transcripts from a gene or genes, or nucleic acids derived therefrom. Transcript processing includes processes such as splicing, editing, modifying and degrading. mRNA including samples include, e.g., mRNA, mRNA transcripts of the gene or genes, cDNA originating from mRNA using reverse transcription, RNA transcribed from amplified DNA, cRNA transcribed from cDNA, DNA amplified from the genes, and the like.

A "container" that may comprise a sample herein is broadly construed to mean any type, shape, or size of container, including a surface, a well, a tube, or a vial. A container is not required to have any particular shape or size to be made out of any specific materials, but merely to act as physical structures that enables analysis or manipulation of tissue located in or on it.

A "stained" slide/substrate herein refers to a substrate that has been treated to assist in revealing differences between ROI samples and other samples so that a pathologist or other trained individual may mark the substrate to denote the outline of any ROIs on the substrate. An "unstained" slide/substrate is a substrate that has not been so treated but that may or may not have been subjected to other types of treatments.

The term "separating" one or more ROIs from X samples on a substrate herein includes means of treating X samples in such a way that it is either physically removed from the substrate, is ablated (e.g., vaporized or burned or physically decomposed), or is chemically treated so that it will not contaminate later analysis of molecules in the ROI sample.

The term "substrate" herein refers to various slides including, but not limited to, FFPE slides, tissue slides, standard slides, containers, stained slides, unstained slides, living tissue, etc.

The term "sample" herein refers to cell tissue, specimens, tissue samples, FFPE tissue, or other biological materials affixed using standard molecular biology methods.

A "computer processor" or "computing means" or "computer" is broadly construed herein to refer to any hardware and/or software combination that will perform the functions required of it. For example, a processor may be a programmable digital microprocessor such as available in the form of an electronic controller, mainframe, server, or personal computer (desktop or portable). Where the processor is programmable, suitable programming can be communicated from a user interface either incorporated into the computer body or at a remote location to the processor, or previously saved in a computer program product (such as a portable or fixed computer readable storage medium, whether magnetic, optical or solid state device based). For example, a magnetic medium or optical disk may carry programming and can be read by a suitable reader communicating with each processor at its corresponding user interface. A "user interface" herein is broadly construed to mean a physical structure that allows a user to program a computer and thus to control certain operations of a system through the computer. Examples include a mainframe or laptop computer keyboard and monitor, other type of visual monitor and keyboard system such as a pad-type or smart-phone type device or other remote device. The user interface may be either physically part of the computer body, located elsewhere in the system, or located remotely from the computer, and able to communicate with the computer processor through a wired or wireless connection.

Methods for Digitally Marking ROIs on Unstained Substrates

Sample analysis and dissection typically involve a series of slides comprising parallel slices of samples. One or more slides in a set may be stained, for example, to reveal individual cell nuclei and/or to help distinguish cells of different types, such as in oncology applications, cancerous and non-cancerous cells. A pathologist may examine a substrate and mark regions of interest (ROIs) on the slide with a pen or other suitable marking device. These ROIs or the associated pen markings may then be mapped (rotated and aligned) with substrate from adjacent slice(s) of sample, that will ultimately be analyzed, such as to extract DNA for genomic sequencing, RNA for RNA expression analysis or to perform in situ analysis of cells, etc. In manual sample dissection methods, the pathologist's pen mark is transferred by hand to a substrate and a razor blade is used to cut out the ROI from surrounding samples on the slide.

Macrodissection techniques, which involve histological sectioning of not only the regions of interest but also surrounding tissues of the organ under investigation, have increasingly been deployed in many pathological investigations, such as tumor typing, diagnosis of inflammatory diseases, and determination of degenerative diseases. In macrodis section, patient tissue of interest ("S" area) are collected from histological specimen, e.g., a glass slide, while excluding the un-needed area ("X" area), so that only the "S" area is used as the input material for the downstream assay. In certain cases, complex "S" shape definition from the Pathologist can result difficult scraping operations from a histo-technician. Often, complex scraping techniques are required, as shown in FIG. 1. The present disclosure relates to systems and methods for processing biological samples such that analytes therein can be more accurately detected, preferably free of interference from non-analytes. Therefore, by improving signal quality and/or reducing noise, the present systems and methods greatly improve outcome of biological assays, especially in the context of analyzing analytes in heterogeneous samples such as FFPE.

By improving assay parameters such as signal quality and reduction of noise, the presently disclosed systems and methods also improve the assay objective, e.g., correlating the presence/absence or levels or activities of biomarkers with a trait of interest, e.g., ethnic trait (for forensics) or disease trait.

The systems and methods of the disclosure are based, in part, on the use of particle micro-blasters to target and remove specified areas of the tissue in a biological specimen (e.g., histology slides) and selectively collect signal-containing ("S") tissue area. The method comprises use of particles and a controlled stream of pressurized air or other gas to direct the particles to the ROI. The method is preferably a dry method, which reduces chances of contamination of the sample and/or dilution of the analytes in the sample.

The presently disclosed methods can be used in a variety of setups. For instance, in a first implementation, wherein macrodissection is desired, the "X" area in the substrate (e.g., histological slide) can be selectively micro-blasted while leaving only the "S" area on the substrate untouched. Afterwards, downstream processing methods can be used to remove the "S" area from the substrate. In a second implementation, wherein macrodissection is also desired, the "S" area in the substrate (e.g., histology slide) may be selectively micro-blasted, while leaving only the "X" area on the substrate untouched. The tissue from the "S" area can be removed from the substrate, and the particles are then gathered into a container to be processed using downstream processing. Yet in another implementation, wherein macrodissection is not needed, all regions of the substrate ("X", and "S" areas) are micro-blasted, and contents of both regions are collected in a container for downstream processing.

Figure 2:
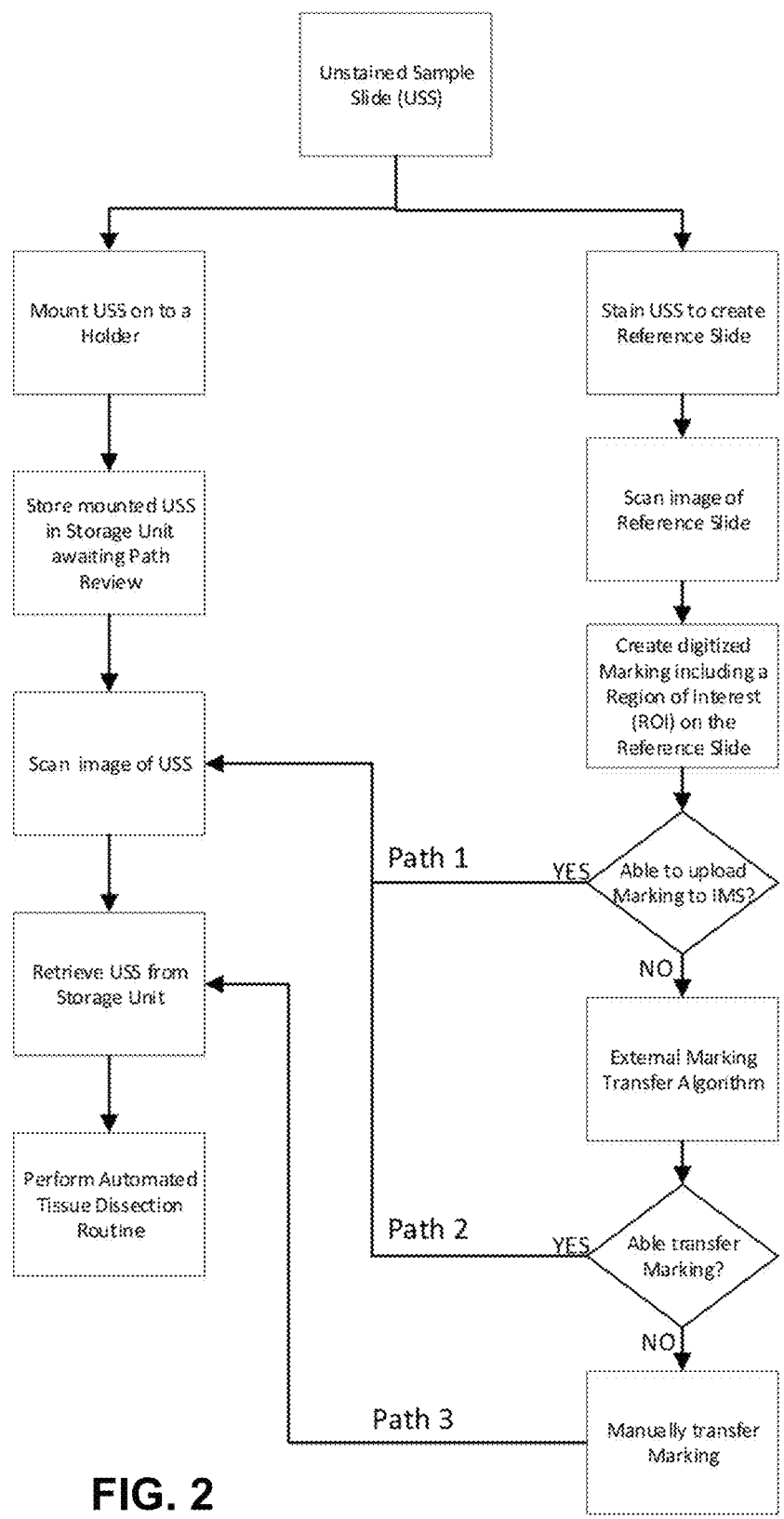
FIG. 2 provides a flowchart showing an exemplary process for digitally processing substrate submissions, in accordance with various embodiments.

FIG. 2 illustrates an exemplary process for digitally processing unstained slide submissions (USS) where the quality and tissue thicknesses cannot be controlled uniformly. The process may include two parallel processes with three paths that may cause the parallel processes to merge.

According to an aspect, along a first parallel path, the USS may be mounted onto a holder. The mounted USS may be stored in a storage unit to await a path review. A scanned image of the USS is created. The USS is retrieved from the storage unit. An automated sample dissection routine may then be performed.

According to an aspect, along a second parallel path, the USS is stained to create a reference slide. The reference slide is scanned to create an image. A digitized marking is created that includes a region of interest (ROI) on the reference slide. It is then determined if the marking is able to be uploaded to an image management system (IMS). If so, then the second parallel path merges with the first parallel path through path 1.

In path 1 the submission substrate(s) successfully transfer their markings through the current digital pathology solution. The USS can be processed earliest in the current digital workflow through path 1.

If not, then an external marking transfer algorithm is applied. If the marking is able to be transferred, then path 2 connects the second parallel path to the first parallel path. For example, in path 2 the submission substrate(s) require development of marking transfer algorithm external to current digital pathology solution. This path is assuming external marking transfer algorithm required (e.g., capability within current digital pathology solution).

Finally, the marking may be manually transferred via path 3. For example, in path 3 direct marking transfer from submission substrate(s) are not available, and require a pathologist to manually perform digital marking on each associated substrate individually. This path is a fall back solution in the case both path 1 and path 2 fail to proceed. The process can still be able to process in automated sample scraping system at a minimum.

Figure 3:
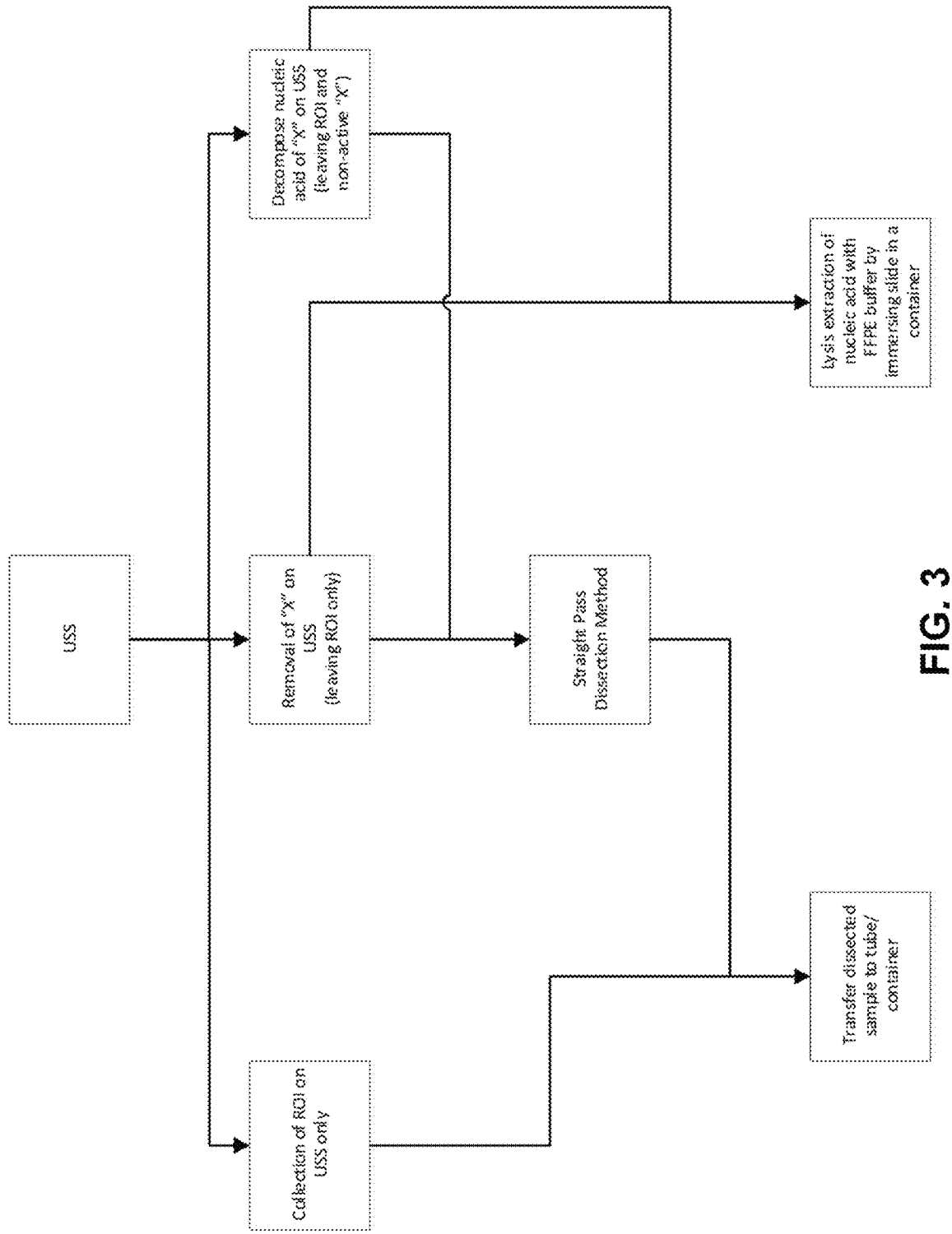
FIG. 3 provides a flow chart showing improved methods for collecting "S" regions or removing "X" regions, in accordance with various embodiments.

FIG. 3 illustrates methods of collecting "S" regions or removing "X" regions. According to an aspect, "X" areas are removed and only "S" areas are left to allow for straight pass (collecting all sample from the slide) methods for sample collection. This is an efficient method as normally there are only small areas of "X". For example, ~50% of cases are straight pass (e.g., no "S" areas). In most cases "X" areas are far less than "S" areas (e.g., less "X" areas to remove).

Additional aspects include decomposing nucleic acids in "X" areas (e.g., only "S" areas and inactive "X" areas left) so that "X" areas do not need to be removed from the substrate. For example, the decomposed "X" areas do not contain any quantifiable DNA/RNA remaining in the "X" area that would further impact analysis. Thus there will be no analyzable quantity of DNA or RNA in the "X" areas.

Further aspects include direct lysis sample on the substrate as a straight pass method. This method can partially break down the cell's phospholipid bilayer and/or fully break down protein to process the sample into liquid lysate suitable for downstream analytical processes. For example, the sample may be exposed to a lysis buffer or buffer solution. Examples of lysing fluids include: hypertonic, hypotonic, pH adjusted solutions, or solutions containing enzymes, such as proteases.

The described processes may be applicable to both automated and manual workflows. For example, they may be implemented in combination with current manual scraping techniques as it is easier to remove or decompose "X" areas than just collecting "S" areas, as there are far more "S" areas than "X" areas.

Sample Dissection Processes

Figure 4:
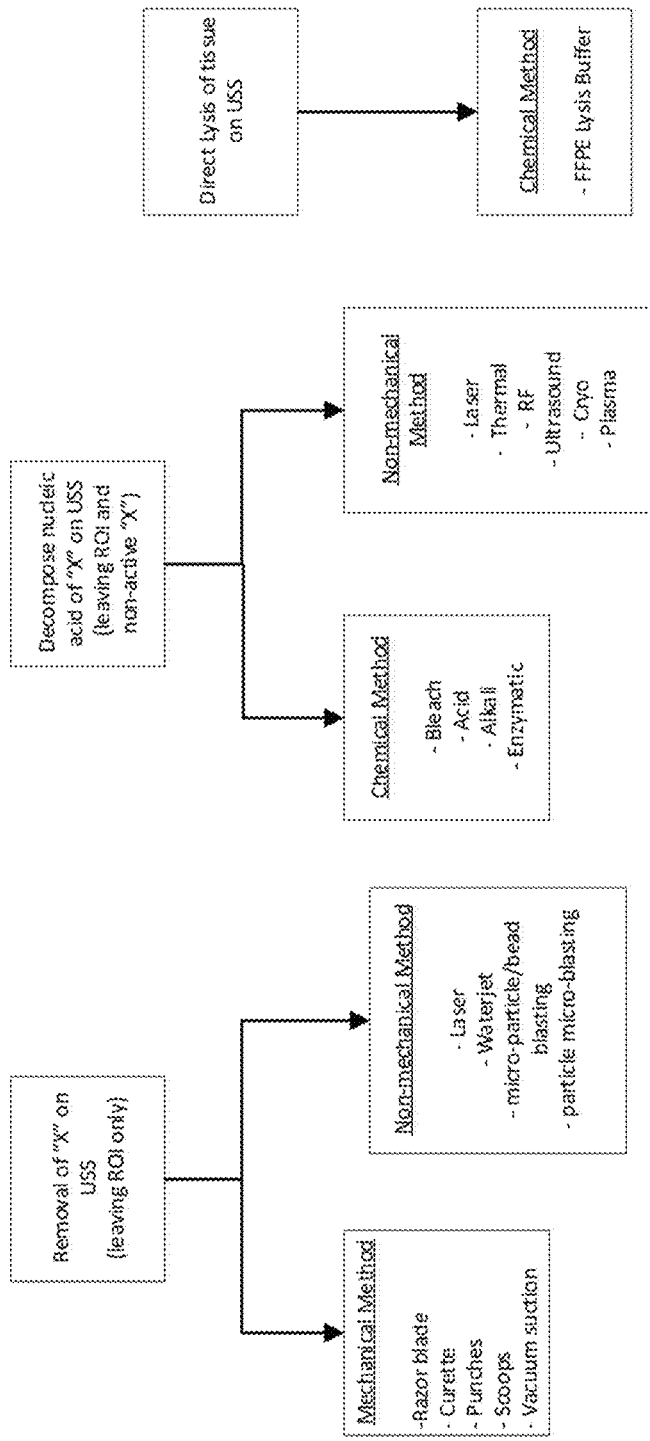
FIG. 4 shows exemplary methods for sample dissection, in accordance with various embodiments.

FIG. 4 illustrates various sample dissections methods. According to aspects of the present disclosure, removal of "X" areas may leave only "S" areas on the slide for collection. For example, all non-desired samples on the substrate may be removed, leaving only desired samples on the slide as a straight pass extraction. To remove the "X" areas, there are mechanical and non-mechanical tools to extract the non-desired samples from the substrates.

Mechanical (e.g., contact) tools may include the use of physical materials, such as razor blade, machine milling (standard or custom milling tools), curette, punches, scoops, microbead blasting and vacuum suction to remove the non-desired sample directly from the substrate. Mechanical tools may further include particle blasting for removing the "X" areas.

Non-mechanical tools may include the use of indirect contact technology, such as laser and water jet, to remove the non-desired sample directly from the substrate. Various laser systems include femto-second laser system, a pico-second laser system, a nano-second laser system, a micro-second laser system, a carbon dioxide laser system, a mode-locked laser system, a pulsed-laser system, a Q-switched laser system, a Nd:YAG laser system, a continuous laser system, a dye-laser system, a tunable laser system, a Ti-Sapphire laser system, a high-power diode laser system, continuous wave laser or a high-power fiber laser system. For example, a femto-second laser system may utilize 20 W average power that has a size of a mid-tower personal computer (PC). Further examples of lasers include, but are not limited to, diode lasers, solid-state lasers, gas lasers, and dye lasers. It is understood that the lasers utilized may be configured to be less powerful to leave less of a footprint than conventional lasers.

Nucleic acid (e.g., DNA) may be decomposed (e.g., denatured) in the "X" areas, leaving only the "S" areas and inactive "X" areas on the slide for collection. For example, decomposing the nucleic acid in the "X" areas will turn those areas inactive to subsequent processes (e.g., nucleic acid content is not at a level in which it will impact gene expression). Therefore, there is no need to physically remove/dissect those areas, and the straight pass sample collection method can be used.

Non-mechanical methods such as laser, thermal, RF, ultrasound, cryogenics, plasma, etc., may be utilized to decompose the non-desired "X" area from the substrate (e.g., glass slide).

Chemical methods may include applying chemicals (e.g., bleach, acid, alkali, and enzyme, etc.) to the "X" areas to decompose the nucleic acid (e.g., DNA/RNA). NaOH or salt may also be utilized to denature the nucleic acid. Additional denaturants may include protein denaturants and nucleic acid denaturants. Exemplary concentrations of bleach may be at least 10% bleach. A combination of chemicals can be combined, including pH adjusted solutions containing endonucleases and/or proteases, or 0.05%-10.0% (weight/volume) of sodium hypochlorite.

According to aspects, using a lysis buffer to directly perform a lysis process on the substrates may bypass the sample dissection process. For example, the substrate with the sample may be directly submerged into a temperature-controlled container with a lysis buffer to separate the entire sample from the substrate. Subsequent protein kinase (Pro K) protein digestion can be performed in the same container and a separate process/container.

According to aspects of the present disclosure, the sample dissection may include mechanical and non-mechanical methods to extract the non-desired sample (e.g., the undesirable "X" area) from the substrates. As described above, a mechanical (contact) method may include the use of physical materials to dissect the non-desired sample directly from the substrate. The system may utilize a physical scraping tool such as particle micro-blasting, sand blasting, razor blade, curette, punches, or scoops combined with a vacuum suction tube next to the scraping action to collect the non-desired sample simultaneously using a suction method.

The suction device consists of a low-cost disposable consumable (e.g. a plastic tube with a filter) to collect all the sample and will be replaced on each case to avoid cross-contamination. Alternatively, a suction device may be cleaned in between samples to eliminate cross-contamination. The filter has the function of stopping the flow of sample but allowing the air to pass through. In addition, the samples cannot fully clog the filter to obstruct the air passage.

The removed sample then can be collected in a waste bin, resulting in leaving only the "S" areas on the substrate for straight pass methods. For example, the straight pass collection can be accomplished by: (a) direct single pass razor blade straight pass that can be easily automated; (b) utilizing a temperature controlled ultrasonic water bath to separate the sample from the substrate into a container/tubes; and/or (c) applying a static charge at the bottom of the collection container/tube after the sample is separated from the substrate.

Non-mechanical methods may include the use of indirect technology (e.g., such as laser and water jet ablation) to dissect the non-desired sample separate from the substrate. For example, laser and waterjet methods may include using a high-pressure waterjet or laser abrasion technology to apply force on the targeted glass surface to separate the sample from the substrate. This results in leaving only the "S" areas on the substrate for straight pass methods.

The straight pass collection can be accomplished by: (a) a direct single pass razor blade straight pass that can be easily automated; (b) utilizing a temperature controlled ultrasonic water bath to separate the sample from the substrate into a container/tubes; and/or (c) applying a static charge at the bottom of the collection container/tube after the sample is separated from the substrate.

To decompose the "X" area, the following methods can be used to extract the non-desired sample from the substrates. For example, non-mechanical methods may decompose the DNA in the non-desired "X" area from the substrate. According to an implementation, the system will be using a non-contact ablation technology such as laser, thermal, RF, ultrasound, cryogenics, or plasma to decompose the non-desired sample from the substrate. This results in leaving only the "S" areas on the substrate for the straight pass method outlined above.

Chemical methods may include applying chemicals to the "X" area to decompose the DNA. For example, the system may apply chemical reagents such as bleach, acid, alkali, or enzyme, etc. on targeted "X" areas on the glass surface to decompose the sample from the substrate. This results in leaving only the "S" areas on the substrate for the straight pass method outlined above.

It is understood that the disclosure is not limited to the pathology space. It can be used for pre-enrichment or isolation target and non-target as well. The technologies identified can also be used separately or in combination with other integrated systems. It is further understood that methods for straight pass may also include the use of pneumatic or a combination of the above methods.

Specimen types include, but are not limited to, cell cultures, frozen sections, fresh sample, liquid biopsy, and cytology samples (i.e. sputum, pleural fluid, etc.). The specimen types can also include non-human targets.

The target specimen also is not limited to a substrate. Any form factor vessel provided as intake to the system which allows the system to image the specimen can be used. Other examples include coverslips (i.e. blood smear generation), bioreactors, cell culture dishes with imaging punches, sample collection paper, or liquid stream/droplets.

Aspects of the present disclosure provide advantages such as being clean, inexpensive, and compatible with high throughput laboratories to extract areas of interest directly from substrates manually (e.g., using pen) or provide an easy-to-use digital annotation tool and object-based algorithm to match digital marking across substrates while maintaining the specimen's morphology that eliminates the need to generate sets of Unstained Substrates (USS) for manual microdis section. It also minimizes risk of operator intervention needed to complete the desired tasks.

In some embodiments, a dissection system may use many means such as laser, water jet, and ultrasound to dissect substrates to separate ROI(s) from unwanted samples.

Some embodiments may include a low-cost mechanical system utilizing milling technology. A small table-top CNC milling machine uses vertical end mill/scooper to collect the pre-defined digital marking for ROI (sample to be saved) or RONI (sample to be discarded) specimen This table-top system will allow user to process one set of slides within a milling enclosure, a vertical milling tool (e.g. low cost rotating scraping fixture with suction feature) will be able to trace and collect specimen the pre-defined end user digital annotation. In some embodiments, the saved sample can be transferred to a tube for subsequent processes. In other embodiments, what is left on the substrate are the S samples, which can be easily and cleanly scraped with a razor blade.

As an example, a large fraction, such as over 40%, of biopsy samples from certain cancers can be all S and no X, while many others have relatively small areas of X. With a small end mill setup, the endmill may have a lumen for suction (i.e., the mill can be a hypotube with or without a grind tip to facilitate ease of machining of the sample). If the X areas are small, one can remove the X areas. If the S areas are small, one can machine and collect the S areas. For simplicity, one may also just consistently remove all X areas or collect all S areas. In some embodiments, a water jet method may alternatively be used to remove the X sample on a slide, leaving the S sample behind.

In other embodiments, the X material is effectively ablated or destroyed on the slide while the S material remains intact. This can be done with various mechanical means such as subjecting the X sample to various energy sources such as particle micro-blasting (e.g., microbead blasting), laser, electrolysis, ultrasound, radio frequency, or thermal energy sources or by selectively freeze-drying the X sample. In some embodiments, the means necessary to ablate the X sample comprises an energy source, e.g. laser, radio-frequency, electric current, sound, or thermal energy source that is capable of lysing cells and/or decomposing biological macromolecules such as nucleic acids and proteins. Some of these methods, for example, may effectively burn and vaporize the X sample. In some embodiments, the apparatus may direct the appropriate energy source precisely to the areas outside of the pen or digitized marking on a substrate, such as focusing a laser or radiofrequency wave or ultrasound wave precisely so that it affects only the X sample areas. For example, in some embodiments, a pulse laser, electrolysis, or ultrasound device may be used as a means to ablate and/or decompose nucleic acid in the X areas from the slide so that only the S areas comprising the ROI(s) remain on the slide. For example, the system may be configured, once the tracing of the S and X areas is performed, to direct a pulse laser, electrolysis, or ultrasound device only to the X areas. For example, the slide may be scanned from one end to the other with the energy from the laser, electrolysis device, or ultrasound device only making contact with the X areas of the slide and thus only ablating cells in the X areas. As a result, the S areas of the slide remain intact and remain the only intact cellular material on the slide. In some embodiments, the energy may effectively vaporize the sample in the X areas and may destroy molecules of interest in those areas such as DNA and RNA so that material from the X areas does not contaminate the resulting isolated S areas in later analysis.

In other embodiments, the X areas may be effectively removed by chemical treatment, including water cavitation methods (e.g., ultrasonic water cavitation methods), such as with one or more agents that decompose the molecules from the sample to be analyzed, such as DNA and/or RNA and/or proteins. Chemical means for decomposing the X sample selectively include, for example, addition of bleach, strong acids, strong bases, or enzymes that target and break down macromolecules such as DNases, RNases, and proteases. For example, a chemical treatment with an RNase or protease enzyme may be directed solely to the X areas of the slide based on the digitized pen markings on the slide. An RNase or protease may, for example, decompose RNA or proteins down to small fragments or monomers. As a result of chemical treatments, for example, the X areas of the slide would not comprise significant levels of intact molecules for analysis, so that an analysis of, for instance, protein or RNA expression levels from the treated sample would reflect only the expression levels in the S portion of the sample since only the protein and/or RNA from the S portion would remain intact.

Either of these methods—ablating the cells of the X portion to effectively remove the X tissue or chemically denaturing the X portion or the molecules of interest therein—may eliminate the need to collect the S tissue by carving it out from a slide containing both X and S tissue. Instead, the entire tissue on the slide may be collected or used for later analysis in a "straight pass" tissue collection approach. In a "straight pass" collection, all of the tissue on the slide is removed and there is no tissue dissection between S and X areas, for example. Accordingly, methods herein are compatible with a straight pass tissue collection in which there is no need to separate S and X tissues on a slide when collecting the tissue for later analysis. Instead, the tissue from the slide may simply be removed from the slide, such as by scraping it off the slide and into a collection vessel, by capillary action, suction, or the like with a rotary cutting tool similar to a milling process. In such embodiments, even if tissue collection is performed manually, there is no need for the highly-skilled razor blade techniques currently in use and that can cause injury or lead to low accuracy. Alternatively, tissue collection may be performed automatically by the instrument. This automation is easier to implement as the objective is to collect all tissue without the need to separate X region from S region. For instance, tissue may be collected into a suitable container such as a well, vial, or tube for processing, such as cell lysis and extraction of molecules of interest such as DNA, RNA, or proteins. Means for mechanically collecting tissue from a treated slide into a container include, for example, sand blasting, using a razor blade or similar blade to scrape off the tissue, or curettes, scoops, punches, or a vacuum to suction off the tissue, addition of solution or another substance to provide a competing medium or surface in comparison to the slide surface such as a charged surface or medium, and the like.

In some embodiments, rather than collecting tissue for analysis into a container such as a well, vial, or tube, for example, certain steps such as cell lysis may be conducted directly on the slide. Again, this may be possible when the X areas are either ablated or denatured to remove or deactivate any significant concentrations of molecules of no interest for the later analysis. In some such embodiments, cell lysis, such as with an appropriate kit, and optionally also extraction of molecules of interest such as DNA, RNA, or proteins may be conducted directly on the tissue slide. In some embodiments, such processes may be automatically controlled by the apparatus. For instance, in some embodiments, the slides may be submerged in a lysis buffer, such as contained in a well or tube or vial so that cell lysis can take place on the slide. In some embodiments, subsequent steps may then be carried out on the submerged slide, such as protease digestion or DNase digestion and/or RNA extraction.

Figure 5:
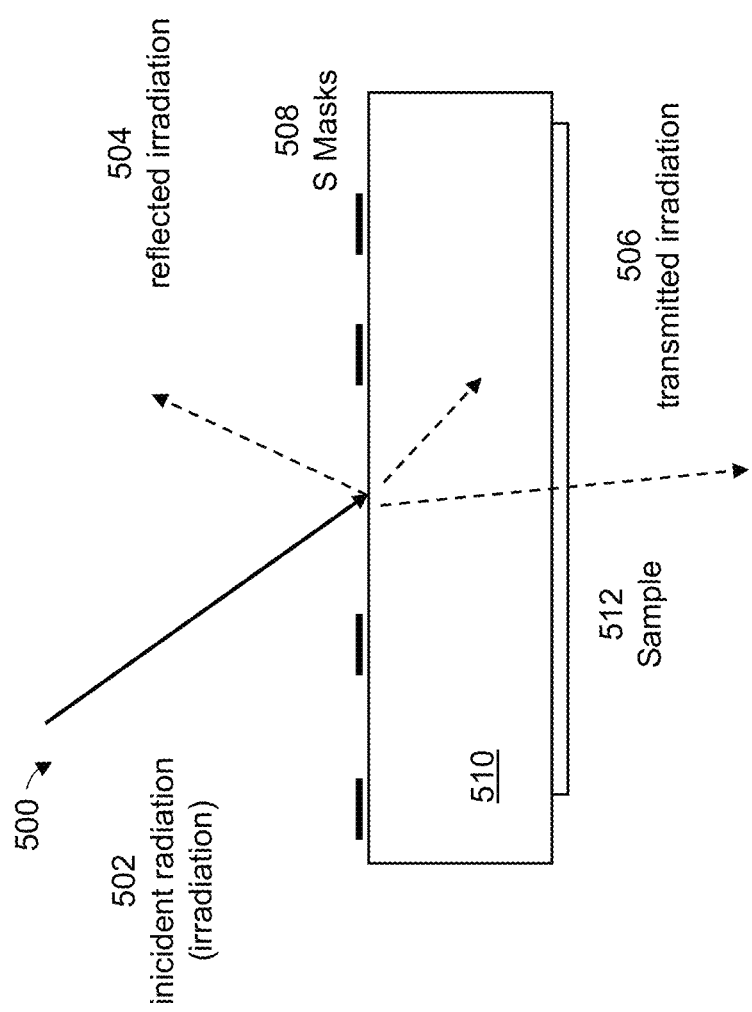
FIG. 5 illustrates exemplary transmitted and reflected irradiation of an incident radiation on a mask, in accordance with various embodiments. This is because the radiation is partially blocked by the mask and the radiation can only reach certain areas (e.g., only a certain percentage of the energy may be transmitted as a function of the wavelength).

FIG. 5 is a diagram 500 of exemplary transmitted irradiation 506 and reflected irradiation 504 of an incident radiation 502 on a mask 508. This is because the radiation 502 is partially blocked by the mask 508 and the transmitted irradiation 506 can only reach certain areas of the sample 512 (e.g., only a certain percentage of the energy may be transmitted as a function of the wavelength). A substrate 510 may be 1 mm thick, which provides some refraction to the transmitted irradiation 506. For example, the mask 508 may be on the top side of the slide 510 such that the radiation 502 is being partially blocked by the mask 508 and the radiation can only reach "X" areas. According to aspects of the present disclosure, the mask 508 may include optical, thermal, mechanical structure, and/or chemical masks to block out the relevant heat, laser, chemical (e.g., microbead blasting), etc. being applied. It is understood that the portions exposed may be either removed or denatured, depending on the process utilized.

Figure 6:
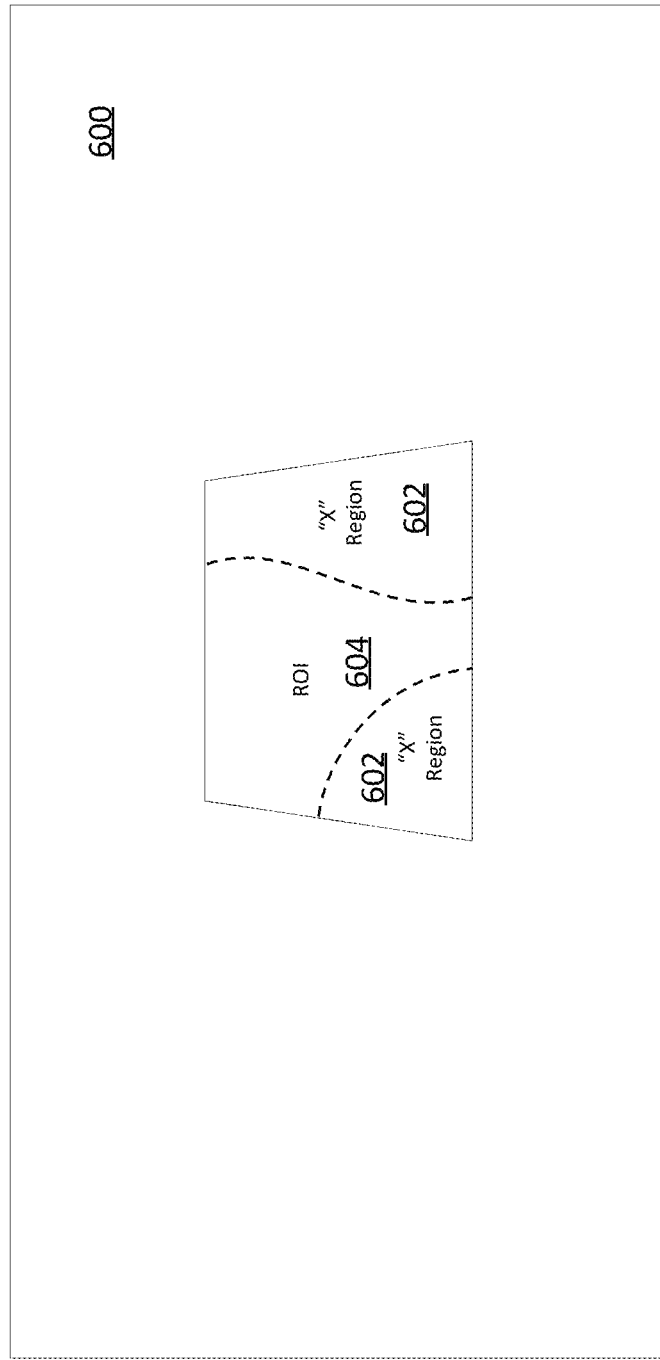
FIG. 6 shows an exemplary slide with undesired "X" regions marked and a region of interest (ROI), in accordance with various embodiments. For example, the "X" regions and the ROI may be determined by the processes described below.

FIG. 6 shows an exemplary slide 600 with undesired "X" regions 602 marked and a region of interest (ROI) 604 (e.g., an "S" region) between the "X" regions 602. For example, the "X" regions 602 and the ROI 604 may be determined by the processes described above.

Figure 7:
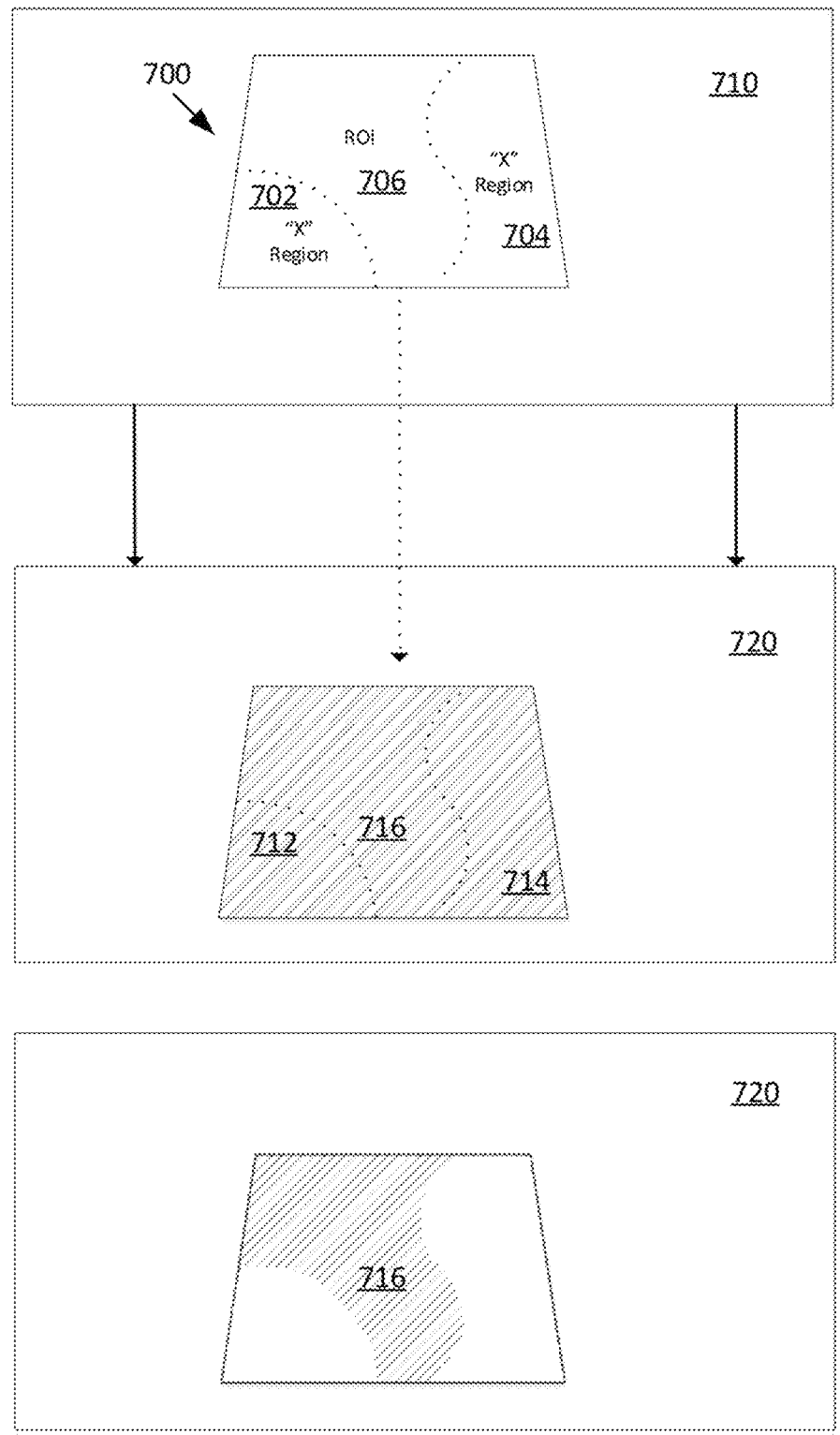
FIG. 7 illustrates a process where undesired "X" regions are removed from a substrate by overlaying a mask over the substrate, in accordance with various embodiments. For example, a mask may be prepared as described below. The mask may be overlaid onto a substrate, and the "X" regions may be removed through various methods, as described below.

FIG. 7 illustrates a process where undesired "X" regions 712 and 714 are removed from a slide 720 by overlaying a mask 700 over the slide 720. For example, a mask slide 710 may be prepared having undesirable "X" regions 702, 704 and desirable "S" region 706 delineated. For example, the "X" regions 702, 704 and the "S" region 706 may be determined by the processes described above. Overlaying the mask 700 over the slide 720 allows for removal of the undesirable "X" regions 712 and 714 from the slide 720 according to the delineated portions. The resulting slide 720 includes only the desired portion 716. It is understood that the "X" regions 712 and 714 may be either removed or denatured, depending on the process utilized.

Figure 10:
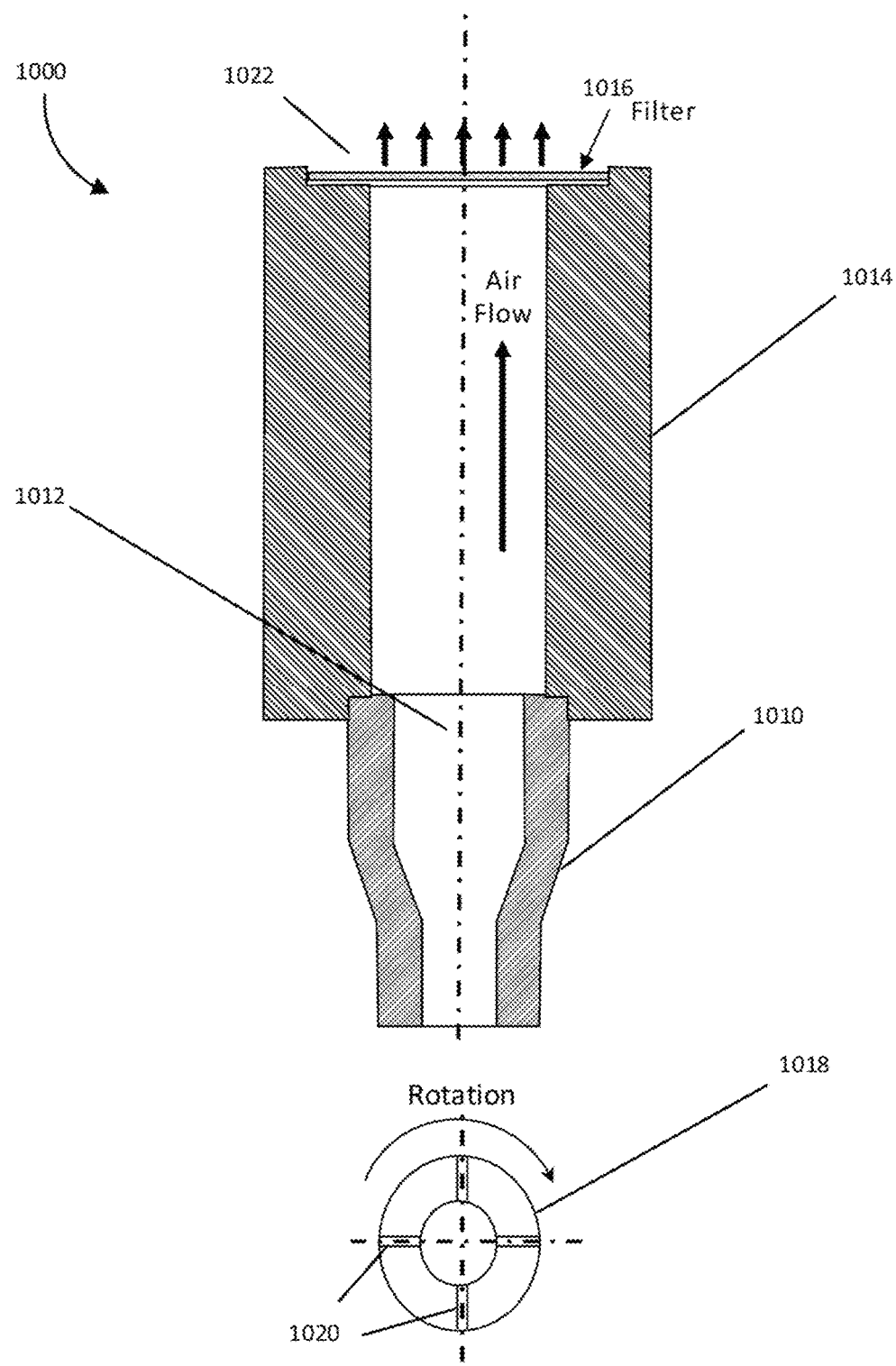
FIG. 10 illustrates an exemplary sample processing device, in accordance with various embodiments.
Figure 11:
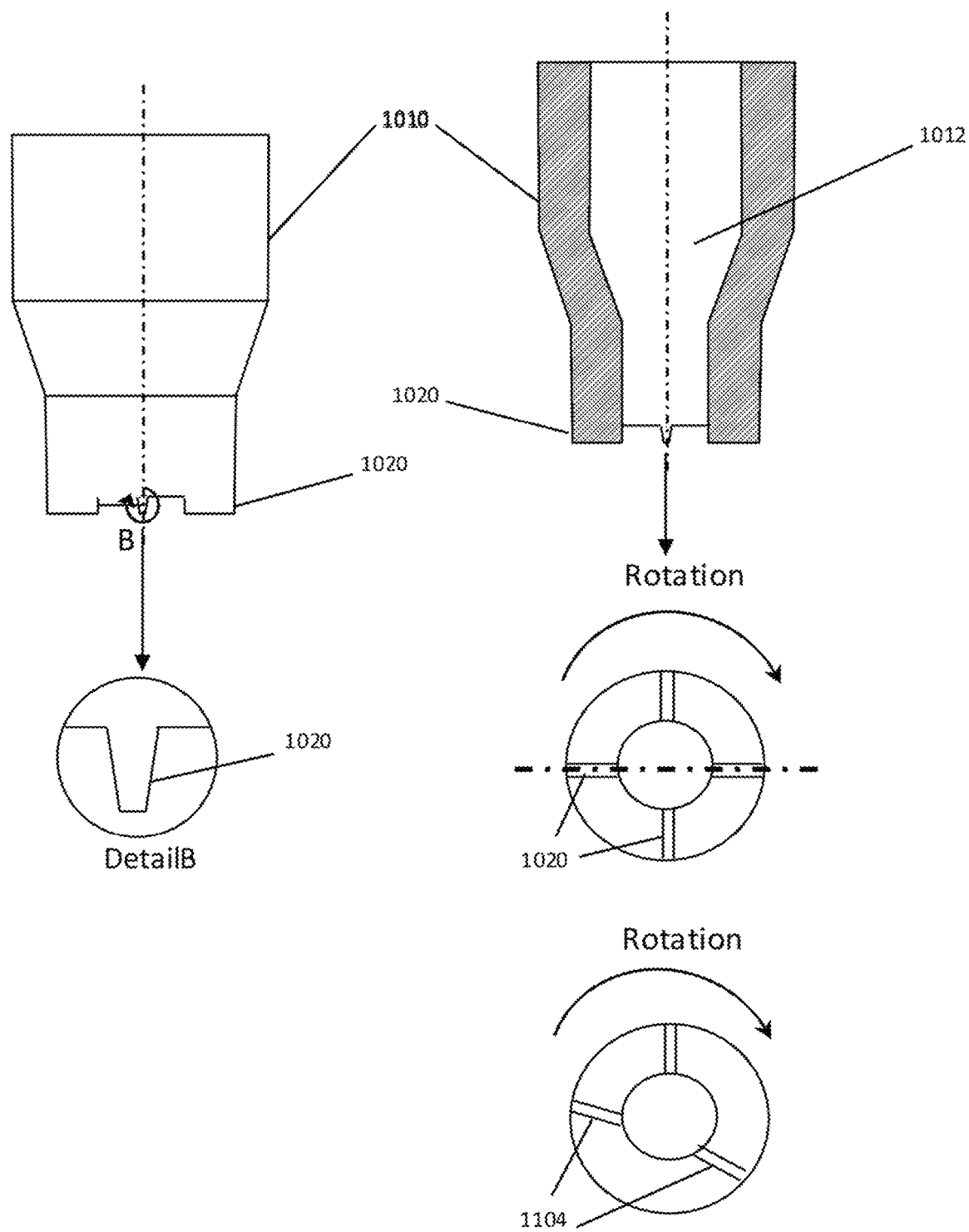
FIG. 11 illustrates an exemplary sample processing device, in accordance with various embodiments.

An exemplary embodiment of the automated tissue dissection (ATD) system utilizes a miniaturized milling system (FIG. 12) with a disposable custom design milling tool as shown in FIG. 10 and FIG. 11 which depicts the distal cutting portion of the milling tool that interfaces with the tissue slide. At the front face of this portion, there can be one or plurality of cutting edges that will dissect tissue from the slide during the rotations of the milling tool. There can be one or more lumens (i.e., channels) in the tool so that the dissected tissue can be forced into the lumen(s) with vacuum suction. The cutting portion can be interfaced with the main body of the tool. The functions of this main body are to house the collected tissue, to interface with the machine chuck, to house the filter element and to interface with the cutting portion. Pressurized air or other inert gases can be used to force the dissected tissue into a collection tube. Alternative embodiments include gravity transfer into a collection tube with agitation, flush buffer through, or directly place the milling tool with collected tissue into the test tube. One disposable milling tool can be used for each case consisting of one or many tissue slides.

To reduce processing time, this custom milling tool is designed to operate at high rotational speeds with direct drive or air-powered. The rotation speed can reach up to or beyond 100,000 rpm. This allows for improved feed rates; therefore, the tool is designed to withstand the operating stresses and temperatures incurred when operating at high rotational speeds.

The distal cutting region can have an inner lumen used to collect tissue ROI and has one or plurality of cutting edges radially dispose at the front face. The material can be steel or any material that is harder than tissue and is conducive to high volume processing with low costs. Engineering plastics may be good choices as they can be injection molded economically. Since the ROI can be as close as 750 microns or smaller for some tissue type, the diameter of this front face can be very small. Small lumens can severely increase the differential pressures across the cutting portion and constrict air flow. It is preferred to quickly taper and step up the lumen size immediately proximal to the cutting interface.

The distal end of the main body interfaces with the cutting portion. The cutting portion may be threaded, insertion molded, bonded, press-fitted or any other suitable assembly technique. The inside of the main body consists of enough volume to house the collected tissues from all the slides in a case. The proximal end is provisioned with features that interfaces with standard machine chucking. The material can be steel or any material that maintains the strength to withstand the operating stresses and is conducive to high volume processing at low costs. Engineering plastics may be good choices as they can be injection molded economically. The proximal end of the main body also has internal features to interface with a filter. It will also have suitable features to interface with vacuum attachment which may be in-line or in an off-axis configuration driven by direct vacuum or via a Venturi device.

The filter element is to stop the collected tissue but allows the air or inert gases to pass through. The filter openings size may be 50 microns or larger. The openings sizes and filter overall size are designed such that the collected tissue will not fully clog the filter at the end of the process. The filter needs to withstand the operating pressures and forces. A pressure relief feature may also be incorporated to prevent clogging. The filter may be bonded or mechanically attached to the main body. An alternative clamping part may also be used.

The distal cutting portion of the milling tool is connected to the main body. The distal cutting portion can contain one or more plurality of cutting edges that interface with the tissue slides. The distal cutting portion design directs dissected tissue toward the center of the cutting portion. The one or more cutting edges at the distal position are oriented radially. Each cutting edge may be straight or curved. The contact angle of the edge and ROI during operation is such that a net vector force will be generated to force the tissue towards the center of the processing element thereby allowing the ROI to be collected. For example, cutting edge #1 can be set to be perpendicular, cutting edge #2 can form an acute angle, and cutting edge #3 can be set at an obtuse angle, each of these positions are set to drive the dissected tissue. The preferred embodiment is to set up a distal cutting portion made up of one or more plurality of edges set up at a minimum like cutting edge #1 and the preferred orientation is set up like cutting edge #2 with an acute angle. The distal cutting portion can be designed to improve cutting power including variations in serration edges and serration positions (including length, width, and depth).

FIG. 10 and FIG. 11 illustrate an exemplary sample milling device, in accordance with various embodiments. As shown herein, the device 1000 is comprised of a first 1014 and second 1010 component. The first component 1014 has openings on opposite ends and the second component 1010 is secured to one end of the first component 1014. The second component 1010 further comprises a sample collection opening 1018 facing away from where the second component 1010 is secured to the first component 1014, the sample collection opening 1018 having one or more sample scraping elements 1020 protruding along a perimeter of the sample collection opening 1018. A vacuum channel 1012 extends through the first 1014 and second 1010 components to connect the sample collection opening 1018 with a vacuum connection opening 1022 on the other end of the first component 1014. When device 1000 is operated to collect sample from a substrate, it is rotated such that the sample scraping elements 1020 mechanically removes portions of the sample from the substrate surface while simultaneously collecting the removed sample portions through the sample collection opening 1018 and vacuum channel 1012 by using a vacuum pump to apply a vacuum to the vacuum connection opening 1022 of the first component 1014. In various embodiments, the removed sample portions can be collected through a filter element 1016 that is attached to the vacuum connection opening 1022. In various embodiments, the removed sample portions is collected in a container that is in fluid communication with the vacuum channel 1012.

In various embodiments, the first 1014 and the second 1010 components are comprised of different materials. In various embodiments, the first 1014 and the second 101 components are comprised of the same materials. Examples of materials that can be used include, but are not limited to: metals, polymers, fiberglass, etc.

In various embodiments, the first 1014 and the second 1010 components are manufactured as a single integrated part and not as two separate individual parts.

In various embodiments, the sample scraping elements 1020 are equally spaced along the perimeter of the sample collection opening 1018. In various embodiments, the sample scraping elements 1104 are differentially spaced along the perimeter of the sample collection opening 1018.

Figure 12:
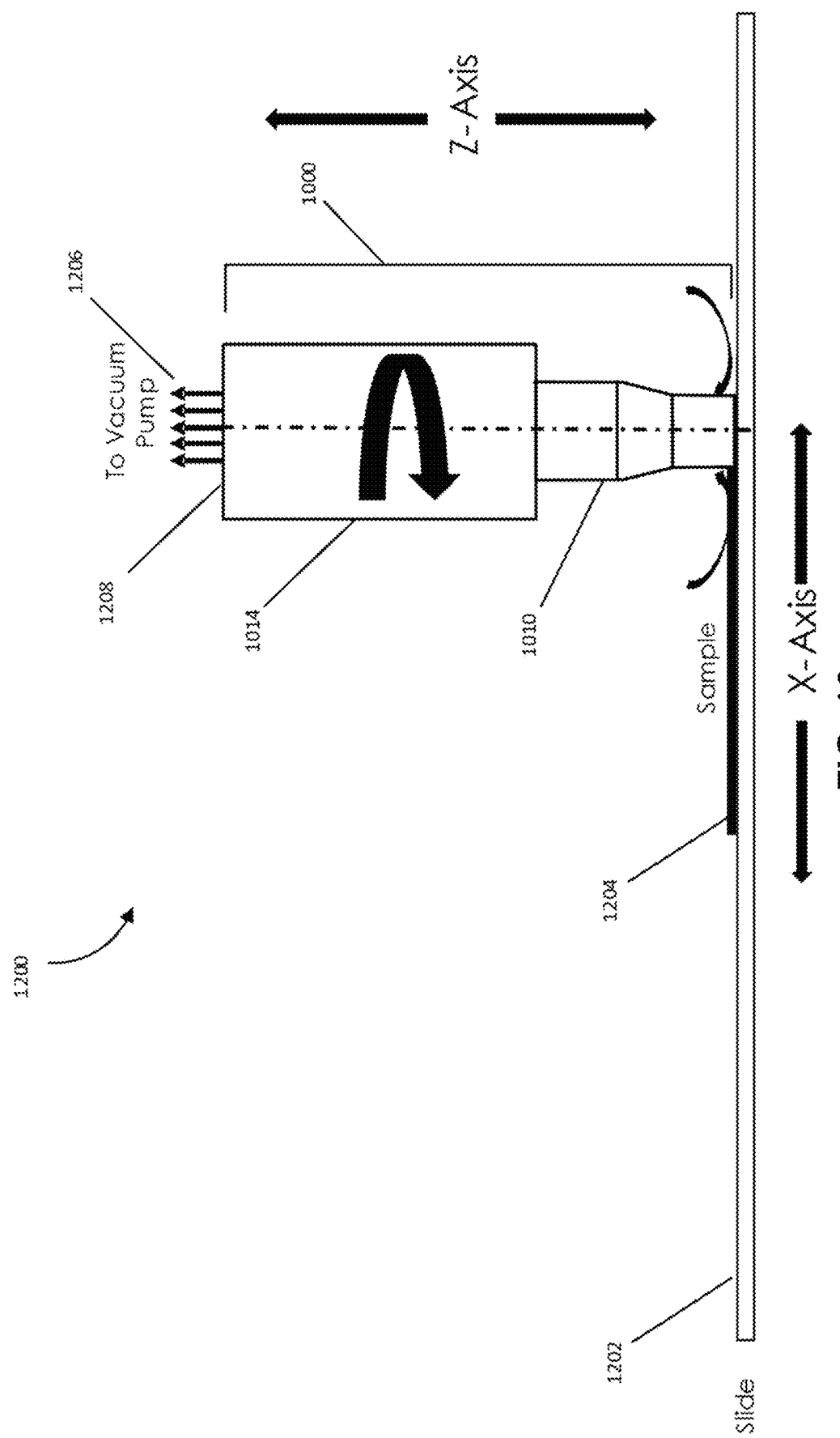
FIG. 12 illustrates an exemplary sample processing system, in accordance with various embodiments.

FIG. 12 illustrates an exemplary sample collection system, in accordance with various embodiments. As depicted herein, the system 1200 includes a sample milling device 1000 that is positioned over a substrate (i.e., slide) 1202 holding a sample 1204. The sample milling device 1000 is comprised of a first 1014 and second 1010 component. When the sample milling device 1000 is being operated, it is rotated and positioned (in an X, Y, and Z axis) such that the tip of the device 1000 contacts the sample 1204 to mechanically remove portions of the sample 1204 from the surface of the substrate 1202 while simultaneously collecting the removed portions of the sample through the use of a vacuum pump 1206 which applies a vacuum to an opening 1208 on one end of the milling device 1000.

In various embodiments, the sample milling device 100 can be moved in an X, Y and Z axis direction such that it only comes into contact with a desired portion of sample 1204. In various embodiments, the slide 1202 holding the sample 1204 can be moved in a X, Y and Z axis direction such that the sample milling device 1000.

In various embodiments, the first 1014 and the second 1010 components are comprised of different materials. In various embodiments, the first 1014 and the second 101 components are comprised of the same materials. Examples of materials that can be used include, but are not limited to: metals, polymers, fiberglass, etc.

Exemplary Subsequent Sample Analysis Procedures

ROI tissue (or S tissue) may be collected so that it can be analyzed or manipulated in various ways. For example, in some embodiments collected ROI tissue is subjected to cell lysis, as described above, followed by one or more other processes. In some embodiments, DNA and/or RNA and/or proteins, cofactors, membrane lipids and the like may be extracted from the ROI tissue either directly or following cell lysis or may be evaluated in situ.

In some embodiments, the systems and methods herein are involved in analysis of DNA in the ROI tissue. For example, systems and methods herein may be used in conjunction with analysis of ROI tissue for copy number variations (CNVs), single nucleotide polymorphisms (SNPs), point mutations in particular genes, detection of deletion or insertion mutations in genes, detection of transpositions, translocations, presence of foreign DNA such as viral or bacterial DNA, methylation of DNA, and the like. In some embodiments, the systems and methods herein may be used in conjunction with analysis of RNA species in the ROI tissue, such as determination of the level of particular RNA transcripts of genes or detection of particular alternatively-spliced RNA transcripts and their relative levels or presence of interfering RNAs. RNA analysis may be performed, for example, by methods including reverse transcription polymerase chain reaction (RT-PCR), such as quantitative RT-PCR, or by whole transcriptome sequencing methods. In some embodiments, the presence or levels of particular proteins in ROI tissue may be evaluated, such as in situ or following cell lysis procedures, by methods such as immunoprecipitation, ELISA, Western blotting, nucleic acids, and the like. In some embodiments, ROI tissue may be evaluated to detect presence or levels of other molecules such as biological cofactors, cellular membrane lipids, or other components and the like.

Figure 8A:
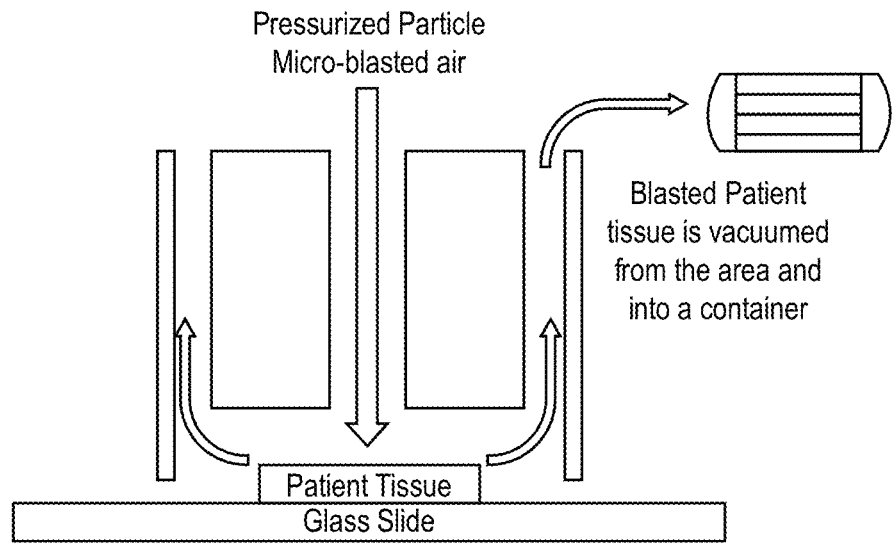
FIGS. 8A and 8B show representative illustrations of the particle micro-blasters, in accordance with various embodiments.
Figure 8B:
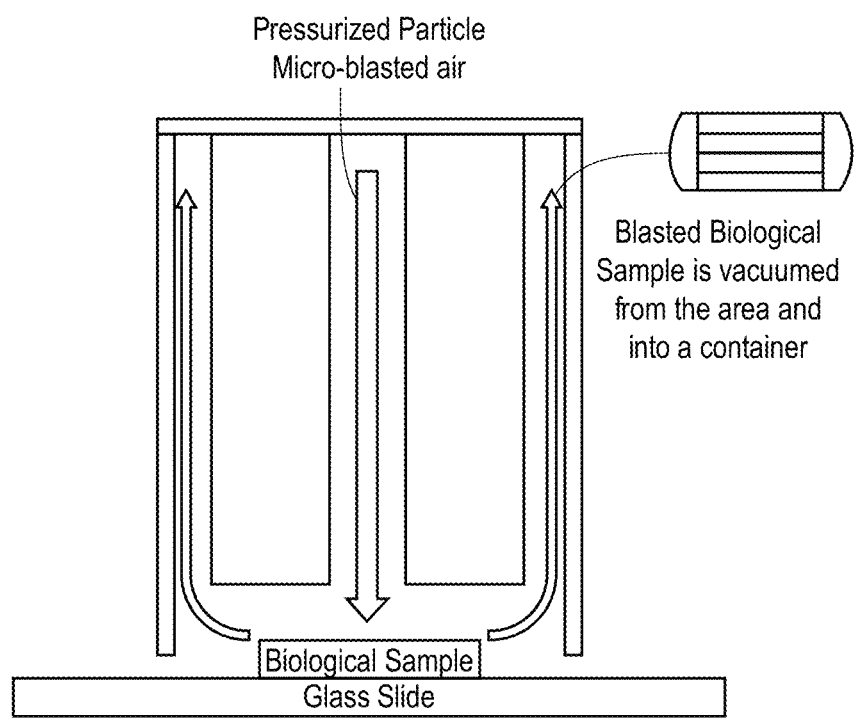

Exemplary systems and methods for analyzing biological samples, e.g., FFPE tissues mounted on glass slides, are shown in FIG. 8A and FIG. 8B.

FIG. 8A shows an exemplary method for the processing and/or analysis of patient samples, e.g., tumor biopsy sample, according to the above-described methods. The biological sample is micro-blasted with a contact medium containing particles and air. In some embodiments, the contact medium may contain particles that are well-suited for use in isolation of specific analytes of interest that are present in the patient sample. For e.g., silica particles or silica coated particles such as silica coated ferromagnetic beads are well suited for isolating nucleic acid markers such as mRNA harboring mis sense mutations or loss of function mutations. The particle micro-blaster is loaded with such particles and the nozzle of the micro-blaster is directed to the desired tissue area. For instance, in the case of pathology specimen, the desired area may be an area containing nucleic acids, e.g., nuclei of cells that have been stained with appropriate stains. Alternately, in cases where the patient specimen contains different tissue types, the desired area may be a tissue type or a tissue layer that contains cells of interest, e.g., epithelial cells lining the pancreatic duct in the case of pancreatic cancer. Micro-blasting the region of interest with the contact medium (containing pressurized air and particles) removes the cells of interest, which are then collected and combined with a tissue lysis buffer to disrupt the cells. This yields a cell lysate solution, wherein the analytes of interest (e.g., in the case of pancreatic cancer, mutant nucleic acids encoding KRAS, TP53, CDKN2A, SMAD4, BRCA1, and/or BRCA2; see Cicenas et al., *Cancers* (Basel), 28, 9(5), 2017) are adsorbed onto the particles. To improve adsorption rate, the pH of the buffer solution may be adjusted at or below the pKa of the surface silanol groups in the silica particles and the salt content of the buffer is increased. The particles are then washed with a solution that leaves the analytes adsorbed on their surface while washing away other components of the lysate solution, e.g., non-analytes such as proteins and lipids. The analytes may be directly analyzed using downstream analytical techniques such as PCR. Alternately, the nucleic acids adsorbed on the surface of silica particles are eluted with a suitable eluent solution prior to downstream analysis with nucleic acid detection techniques such as PCR. Elution is facilitated by using buffers of low ionic strength and pH. If desired, prior to micro-blasting, the sample may be pre-processed using micro-dissection techniques, such as laser micro-dissection, to further refine and/or target the region of interest (ROI).

FIG. 8B shows an exemplary method for the processing and/or analysis of a biological sample, e.g., fixed entomological sample for museum archive or a contact slide containing soil microorganisms, according to the above-described methods. The biological sample is micro-blasted with a contact medium containing particles and air. In some embodiments, the contact medium may contain particles that are well-suited for use in isolation of specific analytes of interest that are present in the patient sample. For e.g., aluminum particles that have been functionalized with amino, carboxyl, sulfonate and phosphate groups may be useful in isolating specific polypeptide markers. The particle micro-blaster is loaded with such particles and the nozzle of the micro-blaster is directed to the desired tissue area. For instance, in the case of fixed insect specimen, the desired area may be an area containing markers of interest, e.g., abdomen. Micro-blasting the region of interest with the contact medium (containing pressurized air and particles) removes the cells of interest, which are then collected and combined with a tissue lysis buffer to disrupt the cells. This yields a cell lysate solution, wherein the analytes of interest are adsorbed onto the particles (e.g., peptides are adsorbed onto functionalized aluminum particles). To improve adsorption rate, depending on the physiochemical properties of the target (e.g., hydrophilicity in case of soluble proteins; hydrophobicity in the case of membrane proteins), the particles may be derivatized. The particles are then washed with a solution that leaves the analytes adsorbed on their surface while washing away other components of the lysate solution, e.g., non-analytes such as lipids. The analytes may be directly analyzed using downstream analytical techniques such as mass spectrometry. Alternately, the polypeptides adsorbed on the surface of aluminum particles are eluted with a suitable eluent solution prior to downstream analysis with peptide detection techniques such as immunoblotting or mass spectrometry. If desired, prior to micro-blasting, the sample may be pre-processed using micro-dissection techniques, such as laser micro-dissection, to further refine and/or target the ROI.

Computer-Implemented Systems

Figure 9:
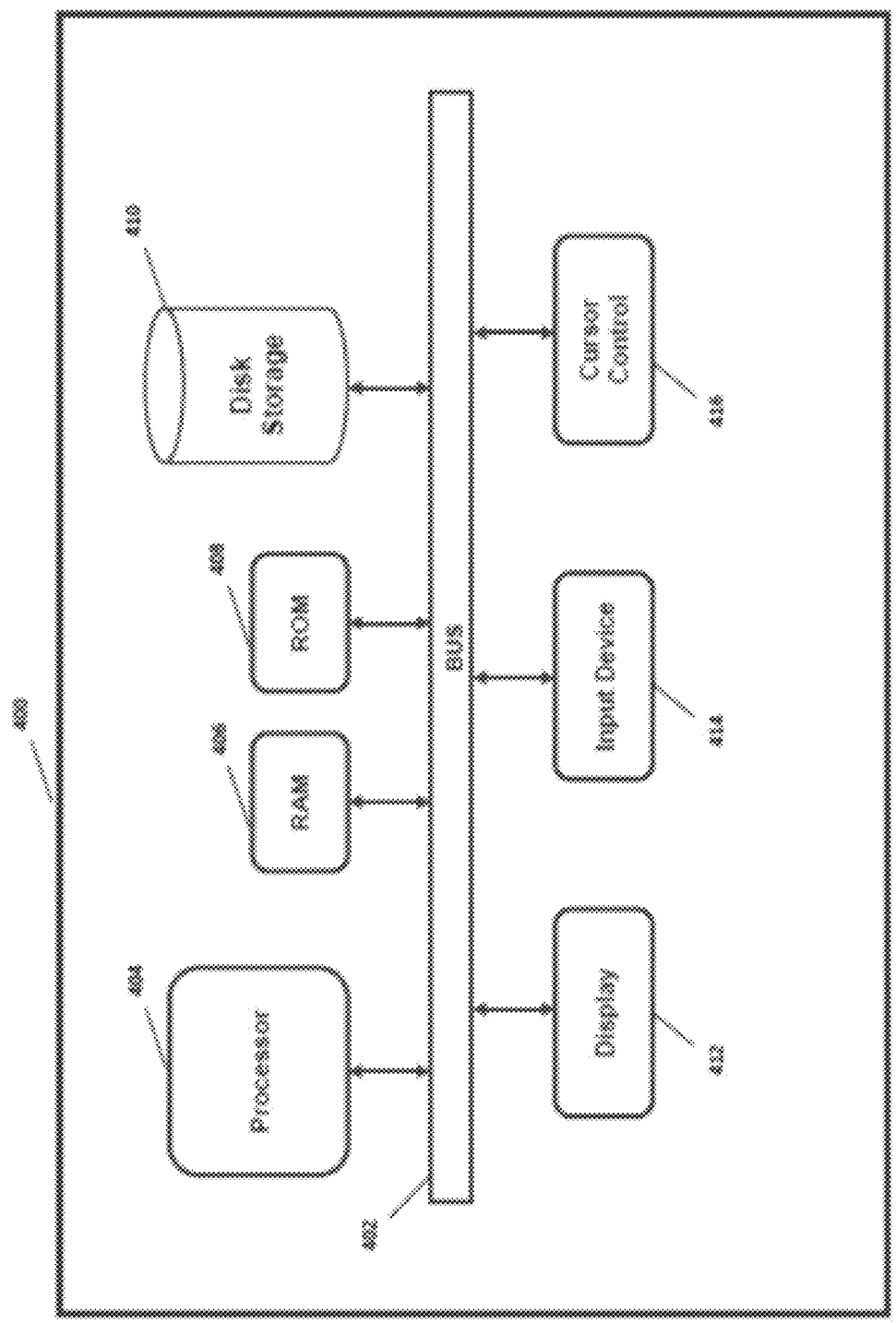
FIG. 9 shows an exemplary system architecture of a computer system for implementation of the described systems and methods.

FIG. 9 is a block diagram that illustrates a computer system 400, upon which embodiments of the present teachings may be implemented. In various embodiments of the present teachings, computer system 400 can include a bus 402 or other communication mechanism for communicating information, and a processor 404 coupled with bus 402 for processing information. In various embodiments, computer system 400 can also include a memory, which can be a random access memory (RAM) 406 or other dynamic storage device, coupled to bus 402 for determining instructions to be executed by processor 404. Memory also can be used for storing temporary variables or other intermediate information during execution of instructions to be executed by processor 404. In various embodiments, computer system 400 can further include a read only memory (ROM) 408 or other static storage device coupled to bus 402 for storing static information and instructions for processor 404. A storage device 410, such as a magnetic disk or optical disk, can be provided and coupled to bus 402 for storing information and instructions.

In various embodiments, computer system 400 can be coupled via bus 402 to a display 412, such as a cathode ray tube (CRT) or liquid crystal display (LCD), for displaying information to a computer user. An input device 414, including alphanumeric and other keys, can be coupled to bus 402 for communicating information and command selections to processor 404. Another type of user input device is a cursor control 416, such as a mouse, a trackball or cursor direction keys for communicating direction information and command selections to processor 404 and for controlling cursor movement on display 412. This input device 414 typically has two degrees of freedom in two axes, a first axis (i.e., x) and a second axis (i.e., y), that allows the device to specify positions in a plane. However, it should be understood that input devices 414 allowing for 3 dimensional (x, y and z) cursor movement are also contemplated herein.

Consistent with certain implementations of the present teachings, results can be provided by computer system 400 in response to processor 404 executing one or more sequences of one or more instructions contained in memory 406. Such instructions can be read into memory 406 from another computer-readable medium or computer-readable storage medium, such as storage device 410. Execution of the sequences of instructions contained in memory 406 can cause processor 404 to perform the processes described herein. Alternatively hard-wired circuitry can be used in place of or in combination with software instructions to implement the present teachings. Thus implementations of the present teachings are not limited to any specific combination of hardware circuitry and software.

The term "computer-readable medium" (e.g., data store, data storage, etc.) or "computer-readable storage medium" as used herein refers to any media that participates in providing instructions to processor 404 for execution. Such a medium can take many forms, including but not limited to, non-volatile media, volatile media, and transmission media. Examples of non-volatile media can include, but are not limited to, optical, solid state, magnetic disks, such as storage device 410. Examples of volatile media can include, but are not limited to, dynamic memory, such as memory 406. Examples of transmission media can include, but are not limited to, coaxial cables, copper wire, and fiber optics, including the wires that comprise bus 402.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In addition to computer readable medium, instructions or data can be provided as signals on transmission media included in a communications apparatus or system to provide sequences of one or more instructions to processor 404 of computer system 400 for execution. For example, a communication apparatus may include a transceiver having signals indicative of instructions and data. The instructions and data are configured to cause one or more processors to implement the functions outlined in the disclosure herein. Representative examples of data communications transmission connections can include, but are not limited to, telephone modem connections, wide area networks (WAN), local area networks (LAN), infrared data connections, NFC connections, etc.

It should be appreciated that the methodologies described herein flow charts, diagrams and accompanying disclosure can be implemented using computer system 400 as a stand-alone device or on a distributed network of shared computer processing resources such as a cloud computing network.

The methodologies described herein may be implemented by various means depending upon the application. For example, these methodologies may be implemented in hardware, firmware, software, or any combination thereof. For a hardware implementation, the processing unit may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

In various embodiments, the methods of the present teachings may be implemented as firmware and/or a software program and applications written in conventional programming languages such as C, C++, Python, etc. If implemented as firmware and/or software, the embodiments described herein can be implemented on a non-transitory computer-readable medium in which a program is stored for causing a computer to perform the methods described above. It should be understood that the various engines described herein can be provided on a computer system, such as computer system 400 of FIG. 9, whereby processor 404 would execute the analyses and determinations provided by these engines, subject to instructions provided by any one of, or a combination of, memory components 406/408/410 and user input provided via input device 414.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical, FLASH memory and non-optical data storage devices. The computer readable medium can also be distributed over a network coupled computer systems so that the computer readable code is stored and executed in a distributed fashion.

EXAMPLES

The structures, materials, compositions, and methods described herein are intended to be representative examples of the disclosure, and it will be understood that the scope of the disclosure is not limited by the scope of the examples. Those skilled in the art will recognize that the disclosure may be practiced with variations on the disclosed structures, materials, compositions and methods, and such variations are regarded as within the ambit of the disclosure.

Example 1: Processing Biological Samples to Obtain Nucleic Acid Analytes

A histology sample containing nucleic acids of interest is processed according to the above-described methods. Here, the contact medium contains particles that are well-suited for use in nucleic acid isolation. These include silica particles or silica coated particles such as silica coated ferromagnetic beads. The particle micro-blaster is loaded with silica particles to provide an efficient way to isolate nucleic acids from tissue specimens. First, the desired tissue area is removed from slides by micro-blasting with silica particles which is then collected and combined with a tissue lysis buffer to disrupt the cells. This yields a cell lysate solution, wherein the nucleic acids are adsorbed onto the silica particles. The silica particles are then washed with a solution that leaves the nucleic acids adsorbed on their surface while washing away other components of the lysate solution such as proteins and lipids. The nucleic acids may be directly analyzed using downstream analytical techniques such as PCR. Alternately, the nucleic acids adsorbed on the surface of silica particles are eluted with a suitable eluent solution prior to downstream analysis with nucleic acid detection techniques such as PCR. If desired, the sample may be pre-processed using micro-dissection techniques such as laser micro-dissection.

Example 2: Processing Biological Samples to Obtain Nucleic Acid and Peptide Analytes Alternatively, the particles used for micro-blasting in Example 1 above are collected in a container and combined with other particles that are optimally suited for selective binding of a variety of potential analytes (e.g., nucleic acids or proteins), and the resulting mixture of particles are used to isolate the analytes of interest. As in Example 1, in this alternate setup, micro-blasting particles that they bind the analyte of interest (e.g., based on charge or hydrophobicity or affinity) are first selected. The mixture of tissue and particles that are generated after micro-blasting are combined with a lysis buffer to disrupt the cells, with the resulting lysate solution then being combined with particles that have oligonucleotides or antibodies bound to their surface, which oligonucleotides or antibodies bind with specificity to the analytes of interest. The particle pairs are then subjected to direct analysis (e.g., chromatography or spectrometry). Alternately, the particle pairs are subjected to a series of steps to binding, washing, and eluting steps to elute the analyte of interest, which is then analyzed using conventional techniques. Lastly, wherein the analyte of interest is a protein, the lysate solution could also be subjected to other analytical steps such as enzyme assays, binding assays, functional assays, etc.

The above-described methods can be combined with any isolation and/or purification steps, which steps may be implemented at any stage of the workflow, preferably prior to the final analytical step, e.g., PCR (in the case of nucleic acid analytes) or ELISA (in the case of protein analytes). For example, nucleic acids of interest are often isolated from tissue by a series of steps comprising (a) tissue lysis, in which the cells of the tissue are disrupted by various methods to break open the cells and release their contents into solution; (b) adsorption of the nucleic acids onto the surface of a solid phase; (c) washing of this solid phase with a solution that leaves the nucleic acids adsorbed to the solid phase but removes other biomolecules: and (d) washing the solid phase with a solution that elutes the nucleic acids from the solid phase, such that the collected eluate contains the isolated nucleic acids. Silica membranes and silica particles are commonly used as the solid phase in this type of process. Other types of particles are commonly used as well, including silica-coated or polymer-coated ferromagnetic beads.

From the foregoing description, one skilled in the art can easily ascertain the essential characteristics of the methods and, without departing from the spirit and scope thereof, can make various changes and modifications to adapt it to various usages and conditions.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described in the foregoing paragraphs. In addition, the materials, methods, and examples are illustrative only and not intended to be limiting. In case of conflict, the present specification, including definitions, will control.

All United States patents and published or unpublished United States patent applications cited herein are incorporated by reference. All published foreign patents and patent applications cited herein are hereby incorporated by reference. All published references, documents, manuscripts, scientific literature cited herein are hereby incorporated by reference. All identifier and accession numbers pertaining to scientific databases referenced herein (e.g., PUBMED, NCBI) are hereby incorporated by reference.

Recitation of Selected Embodiments

Embodiment 1. A system for processing samples affixed onto a substrate, comprising a holder unit for securing a substrate; a camera positioned proximate to the holder unit; a processing element configured to remove a portion of a sample affixed onto the substrate; and a computing device communicatively connected to the holder unit, the camera and the processing element, comprising an image capture engine configured to obtain a first image of a first substrate with a first affixed sample and a second image of a second substrate with a second affixed sample using the camera, a digital marker engine configured to allow a user to generate a marker image that contains the first image and a digital outline of a portion of the first affixed sample, an image overlay engine configured to overlay the marker image onto the second image such that image outlines of the first affixed sample and the second affixed sample are aligned, and a sample removal engine configured to control positioning of the holder unit and the processing element so that only a portion of the second affixed sample that is within the digital outline of the first affixed sample is removed.

Embodiment 2. The system of Embodiment 1, wherein the processing element is configured to remove the portion of the sample utilizing a mechanical tool.

Embodiment 3. The system of Embodiment 2, wherein the mechanical tool comprises at least one of sand blasting, a razor blade, a milling tool, a curette, a hole puncher, a scooper, a vacuum Embodiment 4. The system of any one of Embodiments 1 to 3, wherein the processing element is configured to remove the portion of the sample utilizing a non-mechanical tool.

Embodiment 5. The system of Embodiment 4, wherein the non-mechanical tool comprises at least one of a laser or a waterjet.

Embodiment 6. A method for processing samples affixed onto a substrate, comprising obtaining a first image of a first substrate with a first affixed sample; obtaining a second image of a second substrate with a second affixed sample; generating a marker image containing the first image and a digital outline of a portion of the first affixed sample; overlaying the marker image onto the second image such that image outlines of the first affixed sample and the second affixed sample are aligned; and removing only a portion of the second affixed sample that is within the digital outline of the first affixed using a processing element.

Embodiment 7. The method of Embodiment 6, wherein the removing comprises removing the portion of the second affixed sample with a mechanical tool.

Embodiment 8. The method of Embodiment 6 or Embodiment 7, further comprising removing the portion of the second affixed sample with at least one of sand blasting, a razor blade, a curette, a hole puncher, a scooper, a vacuum, or a combination of above.

Embodiment 9. The method of Embodiment 6, wherein the removing comprises removing the portion of the second affixed sample with a non-mechanical tool.

Embodiment 10. The method of Embodiment 6 or Embodiment 9, further comprising removing the portion of the second affixed sample with at least one of a laser or a waterjet.

Embodiment 11. A system for processing samples affixed onto a substrate, comprising a holder unit for securing a substrate; a camera positioned proximate to the holder unit; a processing element configured to supply a nucleic acid denaturing agent to denature nucleic acid on a portion of a sample affixed onto the substrate; and a computing device communicatively connected to the holder unit, the camera and the processing element, comprising an image capture engine configured to obtain a first image of a first substrate with a first affixed sample and a second image of a second substrate with a second affixed sample using the camera, a digital marker engine configured to allow a user to generate a marker image that contains the first image and a digital outline of a portion of the first affixed sample, an image overlay engine configured to overlay the marker image onto the second image such that image outlines of the first affixed sample and the second affixed sample are aligned, and a nucleic acid denaturing engine configured to control positioning of the holder unit and the processing element so that only nucleic acid in a portion of the second affixed sample that is within the digital outline of the first affixed sample is denatured, the nucleic acid denaturing engine comprising a chemical analyzer for performing chemical analysis, a mass spectrometer, and/or a cell analyzer for performing cell analysis.

Embodiment 12. The system of Embodiment 11, wherein the nucleic acid denaturing agent comprises a chemical.

Embodiment 13. The system of Embodiment 12, wherein the chemical comprises at least one of a bleach, an acid, an alkali, or an enzyme.

Embodiment 14. The system of any one of Embodiments 11 to 13, wherein the processing element is configured to remove the portion of the sample utilizing a non-chemical tool.

Embodiment 15. The system of Embodiment 14, wherein the non-chemical tool comprises at least one of a laser, a thermal heater, radio frequency (RF) waves, ultrasound, cryogenics, or plasma.

Embodiment 16. A method for processing samples affixed onto a substrate, comprising obtaining a first image of a first substrate with a first affixed sample; obtaining a second image of a second substrate with a second affixed sample; generating a marker image containing the first image and a digital outline of a portion of the first affixed sample; overlaying the marker image onto the second image such that image outlines of the first affixed sample and the second affixed sample are aligned; and denaturing nucleic acid in only a portion of the second affixed sample that is within the digital outline of the first affixed sample using a processing element.

Embodiment 17. The method of Embodiment 16, wherein the denaturing comprises exposing the portion of the second affixed sample with a chemical.

Embodiment 18. The method of Embodiment 16 or Embodiment 17, further comprising exposing the portion of the second affixed sample to at least one of a bleach, an acid, an alkali, or an enzyme.

Embodiment 19. The method of Embodiment 16, wherein the denaturing comprises exposing the portion of the second affixed sample with a non-chemical tool.

Embodiment 20. The method of Embodiment 16 or Embodiment 19, further comprising exposing the portion of the second affixed sample to at least one of a laser, a thermal heater, radio frequency (RF) waves, ultrasound, cryogenics, or plasma.

Embodiment 21. A sample processing device, comprising a first component having openings on opposite ends; a second component that is secured to one end of the first component, wherein the second component further comprises a sample collection opening facing away from where the second component is secured to the first component, the sample collection opening having one or more sample scraping elements protruding along a perimeter of the sample collection opening; and a vacuum channel extending through the first and second components to connect the sample collection opening with a vacuum connection opening on the other end of the first component.

Embodiment 22. The sample processing device of Embodiment 21, wherein the first and the second components are comprised of different materials.

Embodiment 23. The sample processing device of Embodiment 22, wherein the first and the second components are comprised of a same material.

Embodiment 24. The sample processing device of any one of Embodiments 21 to 23, wherein the sample scraping elements are equally spaced along the perimeter of the sample collection opening.

Embodiment 25. The sample processing device of any one of Embodiments 21 to 23, wherein the sample scraping elements are differentially spaced along the perimeter of the sample collection opening.

Embodiment 26. The sample processing device of any one of Embodiments 21 to 25, further including a filter that is attached to an opening on one end of the first component.

Embodiment 27. The sample processing device of Embodiment 21, wherein the first and the second components are produced as a single integrated device.

What is claimed:

1. A method of processing a biological sample for a biological assay, comprising (a) contacting the biological sample with a contact medium comprising a particulate substance blasted with pressurized air under conditions sufficient to effectuate blasting of a region of non-interest (RONI) in the biological sample with blasted particulate substance, thereby causing at least partial transfer of the RONI to the contact medium; (b) removing the contact medium from the biological sample; and (c) dissecting a region of interest (ROI) in the biological sample or collecting the remaining biological sample.

2. The method of claim 1, wherein the biological sample is processed for analysis of one or more analytes of diagnostic interest.

3. The method of claim 1, wherein the biological sample comprises punch biopsy specimens, needle biopsy specimens, fresh tissues, tissue cultures, frozen tissue specimen, neutral formalin-treated tissues, organs, organelles, formalin fixed paraffin embedded (FFPE) tissues, ethanol-fixed paraffin-embedded (EFPE) tissues, hematoxylin and eosin (H&E) stained tissues, or glutaraldehyde fixed tissues.

4. The method of claim 1, wherein the biological sample comprises at least one analyte of diagnostic interest selected from genomic DNA (gDNA), methylated DNA, specific methylated DNA, messenger RNA (mRNA), fragmented DNA, fragmented RNA, fragmented mRNA, mitochondrial DNA (mtDNA), chloroplast DNA (ctDNA), viral RNA or viral DNA, microRNA, ribosomal RNA, in situ PCR product, poly A mRNA, RNA/DNA hybrid, lipid, carbohydrate, protein, glycoprotein, lipoprotein, phosphoprotein, specific phosphorylated or acetylated variant of a protein, or viral coat proteins.

5. The method of claim 1, wherein the particulate substance is capable of binding to an analyte or a non-analyte in the biological sample via an interaction selected from ionic interaction, polar-apolar interaction, hydrophobic interaction, van der waal's interaction, chemical coupling, dielectric or zwitterion interaction or a combination thereof.

6. The method of claim 1, wherein the contact medium comprises pressurized air selected from pressurized helium, argon, xenon, nitrogen, carbon dioxide, or a combination thereof.

7. The method of claim 1, wherein the biological sample is mounted on a substrate selected from glass, silicon, poly-L-lysine coated material, nitrocellulose, polystyrene, cyclic olefin copolymers (COCs), cyclic olefin polymers (COPs), polypropylene, polyethylene, and/or polycarbonate.

8. The method of claim 7, wherein the biological sample comprises a nucleic acid analyte and the contact medium comprises a particulate substance comprising silica.

9. The method of claim 1, wherein the dissecting is micro-dissection or laser micro-dissection.

10. The method of claim 1, wherein the contact medium is removed from the biological sample via vacuuming, pressure differential or gradient, gravity, a transport medium including liquid, aerosol, or gas, or a transfer medium selected from magnetic field or electric field.

11. The method of claim 1, comprising collecting the particulate substance in the contact medium; preparing the particulate substance for analysis; and analyzing the particulate substance.

12. The method of claim 11, wherein the preparing the particulate substance for analysis comprises treating the particulate substance with a buffer or lysis buffer and washing the particulate substance to remove non-analytes.

13. The method of claim 11, wherein analysis of the particulate substance comprises polymerase chain reaction (PCR), quantitative PCR (qPCR), reverse transcriptase PCR (RT-PCR), nucleic acid sequence based amplification (NASBA), loop mediated isothermal amplification (LAMP), rolling circle amplification (RCA), immunoassay, immunoPCR (iPCR), enzyme activity assay, staining, imaging, whole genome amplification (WGA), in situ PCR, in situ WGA, colony formation, sequencing, single-molecule sequencing, nanopore analysis, nanopore sequencing, single-molecule imaging, DNA ball formation, electrophoresis, microelectromechanical systems (MEMS) electrophoresis, mass spectrometry, chromatography, HPLC, proximity ligation assay, electrochemical detection, plasmon resonance (SPR), hybridization assay, in situ hybridization assay, fluorescence in situ hybridization (FISH), FRET, cell sorting, FACS, electrochemiluminescence ELISA, or chemiluminescence ELISA.

14. The method of claim 1, wherein the biological sample comprises a two-dimensional tissue including tissue section or slice, or a three-dimensional tissue, including a tissue block comprising a well-defined spatial location of the region of interest (ROI), the region of non-interest (RONI), or both ROI and RONI.

15. A method of assaying for an analyte in a biological sample comprising processing the biological sample by (a) contacting the biological sample with a contact medium comprising a particulate substance blasted with pressurized air under conditions sufficient to effectuate blasting of a region of non-interest (RONI) in the biological sample with blasted particulate substance thereby causing at least partial transfer of the RONI to the contact medium; (b) removing the contact medium from the biological sample to obtain a processed biological sample; (c) dissecting the processed biological sample or collecting the entire process biological sample; and (d) assaying for the analyte in the processed biological sample.

16. The method of claim 1, wherein the particulate substance comprises aluminium oxide; silicon dioxide; metallic-based particles; magnetic or ferromagnetic particles or a combination thereof.

17. The method of claim 15, wherein the particulate substance comprises aluminium oxide; silicon dioxide; metallic-based particles; magnetic or ferromagnetic particles or a combination thereof.

* * * * *